(12) United States Patent
Cho et al.

(10) Patent No.: US 6,987,114 B1
(45) Date of Patent: Jan. 17, 2006

(54) ANTIVIRAL PYRIMIDINEDIONE DERIVATIVES AND PROCESS FOR THE PREPARATION THEREOF

(75) Inventors: Eui-Hwan Cho, Kyungki-do (KR); Sun-Gan Chung, Kyungki-do (KR); Sun-Hwan Lee, Kyungki-do (KR); Ho-Seok Kwon, Kyungki-do (KR); Jae-Eung Lee, Kyungki-do (KR); Jeong-Ho Joo, Kyungki-do (KR)

(73) Assignee: Samjin Pharmaceutical Co., Ltd, Seoul (KR)

( * ) Notice: Subject to any disclaimer, the term of this patent is extended or adjusted under 35 U.S.C. 154(b) by 0 days.

(21) Appl. No.: 09/719,282

(22) PCT Filed: Apr. 8, 2000

(86) PCT No.: PCT/KR00/00328

§ 371 (c)(1),
(2), (4) Date: Oct. 8, 2002

(87) PCT Pub. No.: WO00/61564

PCT Pub. Date: Oct. 19, 2000

(30) Foreign Application Priority Data

Apr. 10, 1999 (KR) ................................ 1999/12629

(51) Int. Cl.
*C07D 239/54* (2006.01)
*C07D 239/60* (2006.01)
*A61K 31/513* (2006.01)

(52) U.S. Cl. ...................... 514/274; 544/309; 544/310; 544/311; 544/314

(58) Field of Classification Search ................ 544/309, 544/310, 311, 314; 514/274
See application file for complete search history.

(56) References Cited

U.S. PATENT DOCUMENTS 5,922,727 A 7/1999 Cho et al. .................... 514/274

6,713,486 B1 * 3/2004 Son et al. .................... 514/269

FOREIGN PATENT DOCUMENTS

| EP | 0 420 763 A2 | 4/1991 |
| WO | WO 95/18109 A1 | 7/1995 |
| WO | WO 97/30979 A1 | 8/1997 |
| WO | WO 00/51990 A1 | 9/2000 |

OTHER PUBLICATIONS

Rajaratnam et al., "Synthesis and Anti-HIV Activity of Acyclic Unsaturated $C_6$- and $C_5$-Thiopenyl Uracil Nucleoside and Nucleotide Analogues," *Pharm. Pharmacol. Commun.*, 1998, pp. 205-209, vol. 4, No. 4.
*Chemical Abstracts*, Abstract No. 109302h, Aug. 31, 1998, p. 667, vol. 129, No. 9.

* cited by examiner

*Primary Examiner*—Deepak Rao
(74) *Attorney, Agent, or Firm*—Birch, Stewart, Kolasch & Birch, LLP

(57) ABSTRACT

The present invention relates to pyrimidinedione derivatives of following formula (I) which are useful as antiviral agents, especially as agents for treatment of AIDS, pharmaceutically acceptable salts thereof, process for the preparation thereof and pharmaceutical compositions containing the same, wherein R represents cyclopropyl; cyclobutyl; cyclohexyl; unsubstituted or mono-, di- or trisubstituted phenyl with a group selected from hydroxy, $C_1$–$C_4$ alkyl, $C_1$–$C_4$ alkoxy, halogen, trifluoromethyl, cyano and amino; 1- or 2-naphthyl; 9-anthracenyl; 2-anthraquinonyl; unsubstituted or substituted pyridyl with a group selected from $C_1$–$C_4$ alkyl, $C_1$–$C_4$ alkoxy, cyano and halogen; 2-, 3- or 4-quinolinyl; oxiranyl; 1-benzotriazolyl; 2-benzoxazolyl; furanyl substituted with $C_1$–$C_4$ alkoxycarbonyl; $C_1$–$C_4$ alkylcarbonyl; or benzoyl, $R_1$ represents halogen or $C_1$–$C_4$ alkyl, $R_2$ and $R_3$ represent independently hydrogen or $C_1$–$C_4$ alkyl, X represents oxygen atom, and Y represents oxygen atom, sulfur atom or carbonyl.

5 Claims, No Drawings

ANTIVIRAL PYRIMIDINEDIONE DERIVATIVES AND PROCESS FOR THE PREPARATION THEREOF

FIELD OF THE INVENTION

The present invention relates to novel pyrimidinedione derivatives or pharmaceutically acceptable salts thereof which are useful as antiviral agents, especially for treatment of AIDS, and process for the preparation thereof.

DESCRIPTION OF THE PRIOR ART

Nowadays, there are about 15 chemotherapeutic agents for AIDS which were approved by the FDA. It has been known that such chemotherapeutic agents have medical action mechanisms to inhibit replication of AIDS virus.

However, they also have drug tolerance and undesirable side effects due to their toxicity. In order to solve these problems, many researches have been carried out to develope new antiviral chemotherapeutic agents with strong antiviral activity as well as lower toxicity.

Much researches to develop new antiviral agents for treatment of AIDS have been focused on pyrimidinedione derivatives, and thus the present inventors have synthesized various new pyrimidinedione derivatives by introducing homocarbocyclic groups to the N-1 position of pyrimidinedione derivatives, which compounds were applied for patent (see, WO97/30979, U.S. Pat. No. 5,922,727), and they continued synthesis and evaluation of new derivatives prepared by introducing new homocarbocyclic groups, aryl and heteroaryl substituents, alkyl and aryl carbonylmethyl groups to the pyrimidinedione derivatives and studied their pharmacological effects. As the result, the inventors have found that the newly synthesized derivatives by the present invention have unexpectedly strong anti-HIV (Human Immunodeficiency Virus) activity as well as very low toxicity.

SUMMARY OF THE INVENTION

Accordingly, an object of the present invention is to provide new pyrimidinedione derivatives of the following formula (I) or pharmaceutically acceptable salts thereof which have strong antiviral activity against HIV.

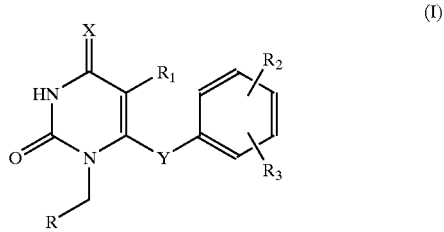

(I)

wherein R represents cyclopropyl; cyclobutyl; cyclohexyl; unsubstituted or mono-, di- or tri-substituted phenyl with a group selected from hydroxy, $C_1$–$C_4$ alkyl, $C_1$–$C_4$ alkoxy, halogen, trifluoromethyl, cyano and amino; 1- or 2-naphthyl; 9-anthracenyl; 2-anthraquinonyl; unsubstituted or substituted pyridyl with a group selected from $C_1$–$C_4$ alkyl, $C_1$–$C_4$ alkoxy, cyano and halogen; 2-, 3- or 4-quinolinyl; oxiranyl; 1-benzotriazolyl; 2-benzoxazolyl; furanyl substituted with $C_1$–$C_4$ alkoxycarbonyl; $C_1$–$C_4$ alkylcarbonyl; or benzoyl, $R_1$ represents halogen or $C_1$–$C_4$ alkyl, $R_2$ and $R_3$ represent independently hydrogen or $C_1$–$C_4$ alkyl, X represents oxygen atom, and Y represents oxygen atom, sulfur atom or carbonyl.

Another object of the invention is to provide a process for the preparation of the compounds of the general formula (I) or pharmaceutically acceptable salts thereof.

The other object of the invention is to provide pharmaceutical preparations having antiviral activity which contains the compound of the general formula (I) or a pharmaceutically acceptable salt thereof as the active ingredient.

DETAILED DESCRIPTION OF THE INVENTION

The compounds of the general formula (I) according to the present invention may be prepared by the following reaction scheme 1.

Scheme 1

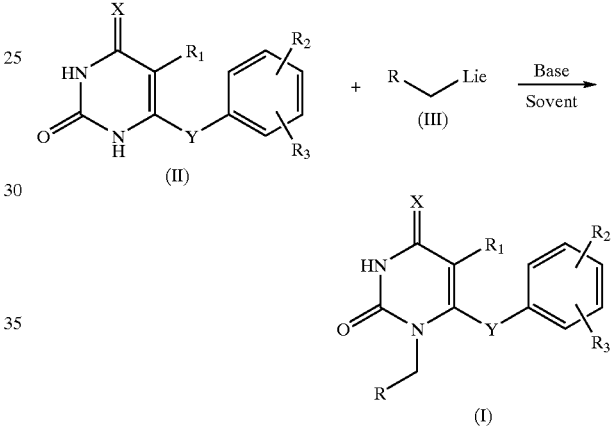

wherein R, $R_1$, $R_2$, $R_3$, X and Y are as defined above, and Lie represents a conventional leaving group such as halogen, alkylsulfonyl and arylsulfonyl.

The compounds of the general formula (I) may be prepared by reacting a compound of the general formula (II) with a compound of the general formula (III) in a conventional organic solvent and in the presence of a base.

The base used in the above reaction may include anhydrous sodium bicarbonate, anhydrous sodium carbonate, sodium hydride and anhydrous potassium carbonate.

The organic solvent used in the reaction may include an organic polar solvent such as dimethylformamide, acetonitrile and dimethylsulfoxide.

In addition, a catalyst such as potassium iodide, lithium iodide or the like may be used.

The reaction may be carried out preferably at the temperature of 10~100° C. for 1–48 hours.

6-substituted pyrimidinedione derivatives of the formula (II) used in the present invention may be prepared as described in WO 93/02044 and WO 95/18109, or by using a similar method thereto.

The compounds of the formula (I) may form an addition salt with a pharmaceutically acceptable inorganic or organic acid or base; for example, bases such as salts of alkali metal and alkaline earth metal including sodium, potassium, magnesium and calcium; inorganic acids such as hydrochloric acid, hydrobromic acid, sulfuric acid, phosphoric acid and nitric acid; organic acids such as formic acid, acetic acid, propionic acid, succinic acid, citric acid, maleic acid, glycolic aicd, lactic acid and malonic acid; amino acids such as serine, cysteine, cystine, asparagine, glutamine, lysine, arginine, leucine and proline; sulfonic acids such as methane sulfonate, ethane sulfonate, benzene sulfonate and toluene sulfonate.

The compounds of the general formula (I) or pharmaceutically acceptable salts thereof may be formulated into conventional pharmaceutical preparations in combination with pharmaceutically acceptable vehicles or carriers, whereby the preparations may be used for treatment or prevention of various viral diseases.

EXAMPLES

The compounds of the general formula (I) defined in the following table were prepared in the following examples.

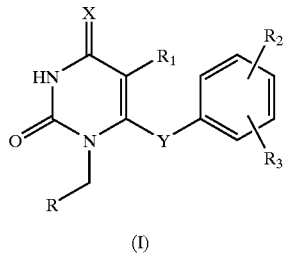

| No. of Example | R | $R_1$ | $R_2$ | $R_3$ | X | Y |
|---|---|---|---|---|---|---|
| 1 | cyclopropylmethyl | Et | Me | Me | O | S |
| 2 | cyclopropylmethyl | iPr | Me | Me | O | S |
| 3 | cyclopropylmethyl | Et | Me | Me | O | O |
| 4 | cyclopropylmethyl | iPr | Me | Me | O | O |
| 5 | cyclopropylmethyl | Et | Me | Me | O | C=O |
| 6 | cyclopropylmethyl | iPr | Me | Me | O | C=O |
| 7 | cyclobutylmethyl | Et | Me | Me | O | S |
| 8 | cyclobutylmethyl | iPr | Me | Me | O | S |
| 9 | cyclobutylmethyl | Et | Me | Me | O | O |
| 10 | cyclobutylmethyl | iPr | Me | Me | O | O |
| 11 | cyclobutylmethyl | Et | Me | Me | O | C=O |
| 12 | cyclobutylmethyl | iPr | Me | Me | O | C=O |
| 13 | cyclohexylmethyl | Et | Me | Me | O | S |
| 14 | cyclohexylmethyl | iPr | Me | Me | O | S |
| 15 | cyclohexylmethyl | Et | Me | Me | O | O |
| 16 | cyclohexylmethyl | iPr | Me | Me | O | O |
| 17 | cyclohexylmethyl | Et | Me | Me | O | C=O |
| 18 | cyclohexylmethyl | iPr | Me | Me | O | C=O |
| 19 | pyridylmethyl | Et | Me | Me | O | S |
| 20 | benzyl | iPr | Me | Me | O | S |
| 21 | benzyl | Et | Me | Me | O | O |
| 22 | benzyl | iPr | Me | Me | O | O |

-continued

[Structure (I): pyrimidine core with X=, R₁, R₂, R₃, Y, R substituents]

(I)

| No. of Example | R | R₁ | R₂ | R₃ | X | Y |
|---|---|---|---|---|---|---|
| 23 | phenyl | Et | Me | Me | O | C=O |
| 24 | phenyl | iPr | Me | Me | O | C=O |
| 25 | 3-OCH₃-phenyl | Et | Me | Me | O | S |
| 26 | 3-OCH₃-phenyl | iPr | Me | Me | O | S |
| 27 | 3-OCH₃-phenyl | Et | Me | Me | O | O |
| 28 | 3-OCH₃-phenyl | iPr | Me | Me | O | O |
| 29 | 3-OCH₃-phenyl | Et | Me | Me | O | C=O |
| 30 | 3-OCH₃-phenyl | iPr | Me | Me | O | C=O |

-continued

[Structure (I): same as above]

(I)

| No. of Example | R | R₁ | R₂ | R₃ | X | Y |
|---|---|---|---|---|---|---|
| 31 | 4-F₃CO-phenyl | Et | Me | Me | O | S |
| 32 | 4-F₃CO-phenyl | iPr | Me | Me | O | S |
| 33 | 4-F₃CO-phenyl | Et | Me | Me | O | O |
| 34 | 4-F₃CO-phenyl | iPr | Me | Me | O | O |
| 35 | 4-F₃CO-phenyl | Et | Me | Me | O | C=O |
| 36 | 4-F₃CO-phenyl | iPr | Me | Me | O | C=O |
| 37 | 2-CN-phenyl | Et | Me | Me | O | S |
| 38 | 2-CN-phenyl | iPr | Me | Me | O | S |
| 39 | 2-CN-phenyl | Et | Me | Me | O | O |
| 40 | 2-CN-phenyl | iPr | Me | Me | O | O |

-continued (I) — structure with X, R₁, R₂, R₃, Y, R substituents on pyrimidine ring.

| No. of Example | R | R₁ | R₂ | R₃ | X | Y |
|---|---|---|---|---|---|---|
| 41 | 2-cyanophenyl (o-Me, CN) | Et | Me | Me | O | C=O |
| 42 | 2-cyanophenyl | iPr | Me | Me | O | C=O |
| 43 | 3-cyanophenyl | Et | Me | Me | O | S |
| 44 | 3-cyanophenyl | iPr | Me | Me | O | S |
| 45 | 3-cyanophenyl | Et | Me | Me | O | O |
| 46 | 3-cyanophenyl | iPr | Me | Me | O | O |
| 47 | 3-cyanophenyl | Et | Me | Me | O | C=O |
| 48 | 3-cyanophenyl | iPr | Me | Me | O | C=O |
| 49 | 3,5-dimethylphenyl | Et | Me | Me | O | S |
| 50 | 3,5-dimethylphenyl | iPr | Me | Me | O | S |
| 51 | 3,5-dimethylphenyl | Et | Me | Me | O | O |
| 52 | 3,5-dimethylphenyl | iPr | Me | Me | O | O |
| 53 | 3,5-dimethylphenyl | Et | Me | Me | O | C=O |
| 54 | 3,5-dimethylphenyl | iPr | Me | Me | O | C=O |
| 55 | 3,5-dimethoxyphenyl | Et | Me | Me | O | S |

-continued

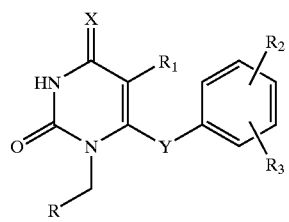

(I)

| No. of Example | R | R$_1$ | R$_2$ | R$_3$ | X | Y |
|---|---|---|---|---|---|---|
| 56 | 3,5-(CH$_3$O)$_2$-C$_6$H$_3$ | iPr | Me | Me | O | S |
| 57 | 3,5-(CH$_3$O)$_2$-C$_6$H$_3$ | Et | Me | Me | O | O |
| 58 | 3,5-(CH$_3$O)$_2$-C$_6$H$_3$ | iPr | Me | Me | O | O |
| 59 | 3,5-(CH$_3$O)$_2$-C$_6$H$_3$ | Et | Me | Me | O | C=O |
| 60 | 3,5-(CH$_3$O)$_2$-C$_6$H$_3$ | iPr | Me | Me | O | C=O |
| 61 | 3,5-(F$_3$C)$_2$-C$_6$H$_3$ | Et | Me | Me | O | S |
| 62 | 3,5-(F$_3$C)$_2$-C$_6$H$_3$ | iPr | Me | Me | O | S |

-continued

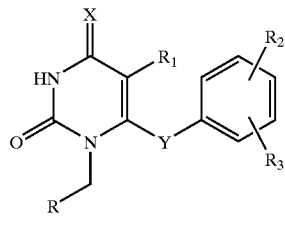

(I)

| No. of Example | R | R$_1$ | R$_2$ | R$_3$ | X | Y |
|---|---|---|---|---|---|---|
| 63 | 3,5-(F$_3$C)$_2$-C$_6$H$_3$ | Et | Me | Me | O | O |
| 64 | 3,5-(F$_3$C)$_2$-C$_6$H$_3$ | iPr | Me | Me | O | O |
| 65 | 3,5-(F$_3$C)$_2$-C$_6$H$_3$ | Et | Me | Me | O | C=O |
| 66 | 3,5-(F$_3$C)$_2$-C$_6$H$_3$ | iPr | Me | Me | O | C=O |
| 67 | 2,5-F$_2$-C$_6$H$_3$ | Et | Me | Me | O | S |
| 68 | 2,5-F$_2$-C$_6$H$_3$ | iPr | Me | Me | O | S |
| 69 | 2,5-F$_2$-C$_6$H$_3$ | Et | Me | Me | O | O |
| 70 | 2,5-F$_2$-C$_6$H$_3$ | iPr | Me | Me | O | O |
| 71 | 2,5-F$_2$-C$_6$H$_3$ | Et | Me | Me | O | C=O |

-continued
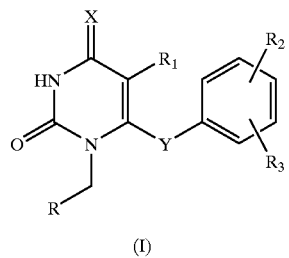
(I)
| No. of Example | R | R₁ | R₂ | R₃ | X | Y |
|---|---|---|---|---|---|---|
| 72 | 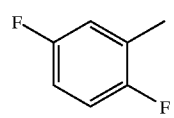 | iPr | Me | Me | O | C=O |
| 73 | 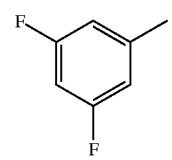 | Et | Me | Me | O | S |
| 74 | 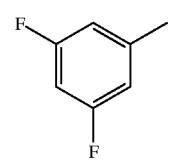 | iPr | Me | Me | O | S |
| 75 | 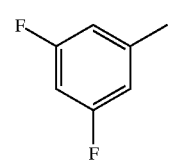 | Et | Me | Me | O | O |
| 76 | 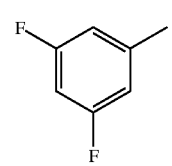 | iPr | Me | Me | O | O |
| 77 | 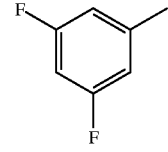 | Et | Me | Me | O | C=O |
| 78 | 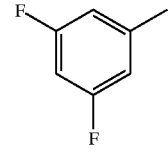 | iPr | Me | Me | O | C=O |
| 79 | 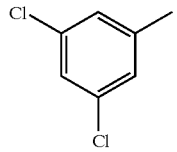 | Et | Me | Me | O | S |
-continued
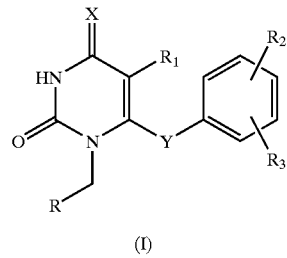
(I)
| No. of Example | R | R₁ | R₂ | R₃ | X | Y |
|---|---|---|---|---|---|---|
| 80 | 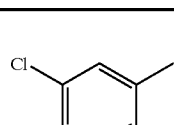 | iPr | Me | Me | O | S |
| 81 | 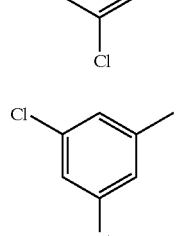 | Et | Me | Me | O | O |
| 82 | 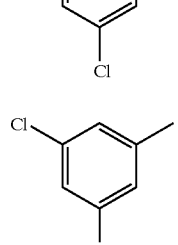 | iPr | Me | Me | O | O |
| 83 | Cl-phenyl-Cl | Et | Me | Me | O | C=O |
| 84 | Cl-phenyl-Cl | iPr | Me | Me | O | C=O |
| 85 | Br-phenyl-Br | Et | Me | Me | O | S |
| 86 | Br-phenyl-Br | iPr | Me | Me | O | S |

-continued

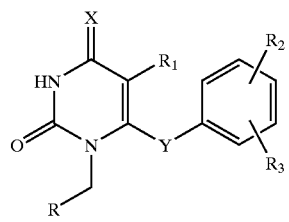

(I)

| No. of Example | R | R₁ | R₂ | R₃ | X | Y |
|---|---|---|---|---|---|---|
| 87 | 3,5-dibromophenyl | Et | Me | Me | O | O |
| 88 | 3,5-dibromophenyl | iPr | Me | Me | O | O |
| 89 | 3,5-dibromophenyl | Et | Me | Me | O | C=O |
| 90 | 3,5-dibromophenyl | iPr | Me | Me | O | C=O |
| 91 | 2-naphthyl | Et | Me | Me | O | S |
| 92 | 2-naphthyl | iPr | Me | Me | O | S |
| 93 | 2-naphthyl | Et | Me | Me | O | O |
| 94 | 2-naphthyl | iPr | Me | Me | O | O |
| 95 | 2-naphthyl | Et | Me | Me | O | C=O |

-continued

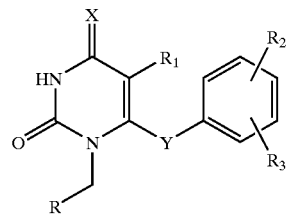

(I)

| No. of Example | R | R₁ | R₂ | R₃ | X | Y |
|---|---|---|---|---|---|---|
| 96 | 2-naphthyl | iPr | Me | Me | O | C=O |
| 97 | 9-anthryl | Et | Me | Me | O | S |
| 98 | 9-anthryl | iPr | Me | Me | O | S |
| 99 | 9-anthryl | Et | Me | Me | O | O |
| 100 | 9-anthryl | iPr | Me | Me | O | O |
| 101 | 9-anthryl | Et | Me | Me | O | C=O |
| 102 | 9-anthryl | iPr | Me | Me | O | C=O |
| 103 | 2-anthraquinonyl | Et | Me | Me | O | S |

-continued

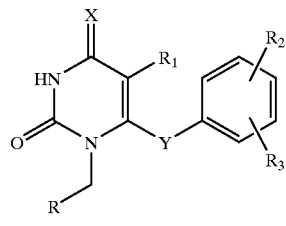

(I)

| No. of Example | R | R₁ | R₂ | R₃ | X | Y |
|---|---|---|---|---|---|---|
| 104 | 2-methylanthraquinonyl | iPr | Me | Me | O | S |
| 105 | 2-methylanthraquinonyl | Et | Me | Me | O | O |
| 106 | 2-methylanthraquinonyl | iPr | Me | Me | O | O |
| 107 | 2-methylanthraquinonyl | Et | Me | Me | O | C=O |
| 108 | 2-methylanthraquinonyl | iPr | Me | Me | O | C=O |
| 109 | 2-pyridylmethyl | Et | Me | Me | O | S |
| 110 | 2-pyridylmethyl | iPr | Me | Me | O | S |

-continued

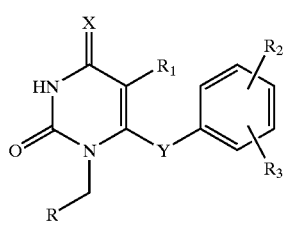

(I)

| No. of Example | R | R₁ | R₂ | R₃ | X | Y |
|---|---|---|---|---|---|---|
| 111 | 2-pyridylmethyl | Et | Me | Me | O | O |
| 112 | 2-pyridylmethyl | iPr | Me | Me | O | O |
| 113 | 2-pyridylmethyl | Et | Me | Me | O | C=O |
| 114 | 2-pyridylmethyl | iPr | Me | Me | O | C=O |
| 115 | 3-pyridylmethyl | Et | Me | Me | O | S |
| 116 | 3-pyridylmethyl | iPr | Me | Me | O | S |
| 117 | 3-pyridylmethyl | Et | Me | Me | O | O |
| 118 | 3-pyridylmethyl | iPr | Me | Me | O | O |
| 119 | 3-pyridylmethyl | Et | Me | Me | O | C=O |
| 120 | 3-pyridylmethyl | iPr | Me | Me | O | C=O |

-continued

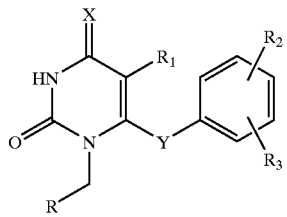

(I)

| No. of Example | R | R₁ | R₂ | R₃ | X | Y |
|---|---|---|---|---|---|---|
| 121 | 6-chloropyridin-2-yl-methyl | Et | Me | Me | O | S |
| 122 | 6-chloropyridin-2-yl-methyl | iPr | Me | Me | O | S |
| 123 | 6-chloropyridin-2-yl-methyl | Et | Me | Me | O | O |
| 124 | 6-chloropyridin-2-yl-methyl | iPr | Me | Me | O | O |
| 125 | 6-chloropyridin-2-yl-methyl | Et | Me | Me | O | C=O |
| 126 | 6-chloropyridin-2-yl-methyl | iPr | Me | Me | O | C=O |
| 127 | 6-bromopyridin-2-yl-methyl | Et | Me | Me | O | O |
| 128 | 6-bromopyridin-2-yl-methyl | iPr | Me | Me | O | O |

-continued

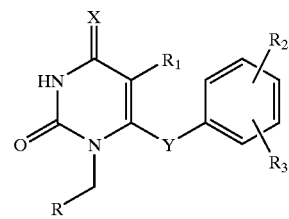

(I)

| No. of Example | R | R₁ | R₂ | R₃ | X | Y |
|---|---|---|---|---|---|---|
| 129 | 6-bromopyridin-2-yl-methyl | Et | Me | Me | O | C=O |
| 130 | 6-bromopyridin-2-yl-methyl | iPr | Me | Me | O | C=O |
| 131 | quinolin-2-yl-methyl | Et | Me | Me | O | S |
| 132 | quinolin-2-yl-methyl | iPr | Me | Me | O | S |
| 133 | quinolin-2-yl-methyl | Et | Me | Me | O | O |
| 134 | quinolin-2-yl-methyl | iPr | Me | Me | O | O |
| 135 | quinolin-2-yl-methyl | Et | Me | Me | O | C=O |
| 136 | quinolin-2-yl-methyl | iPr | Me | Me | O | C=O |
| 137 | oxiranyl-methyl | Et | Me | Me | O | O |
| 138 | oxiranyl-methyl | iPr | Me | Me | O | O |
| 139 | oxiranyl-methyl | Et | Me | Me | O | C=O |

-continued

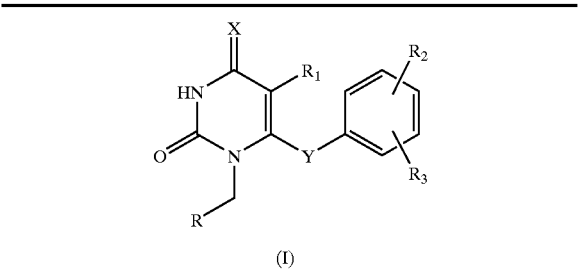

(I)

| No. of Example | R | R₁ | R₂ | R₃ | X | Y |
|---|---|---|---|---|---|---|
| 140 | (oxirane) | iPr | Me | Me | O | C=O |
| 141 | 1-methylbenzotriazole | Et | Me | Me | O | O |
| 142 | 1-methylbenzotriazole | iPr | Me | Me | O | O |
| 143 | 1-methylbenzotriazole | Et | Me | Me | O | C=O |
| 144 | 1-methylbenzotriazole | iPr | Me | Me | O | C=O |
| 145 | benzoxazol-2-ylmethyl | Et | Me | Me | O | S |
| 146 | benzoxazol-2-ylmethyl | iPr | Me | Me | O | S |
| 147 | benzoxazol-2-ylmethyl | Et | Me | Me | O | O |
| 148 | benzoxazol-2-ylmethyl | iPr | Me | Me | O | O |
| 149 | benzoxazol-2-ylmethyl | Et | Me | Me | O | C=O |
| 150 | benzoxazol-2-ylmethyl | iPr | Me | Me | O | C=O |

-continued

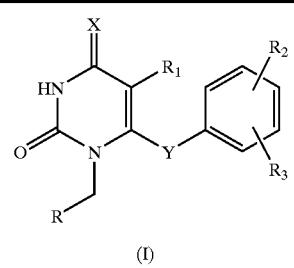

(I)

| No. of Example | R | R₁ | R₂ | R₃ | X | Y |
|---|---|---|---|---|---|---|
| 151 | methyl 2-methylfuran-3-carboxylate | Et | Me | Me | O | S |
| 152 | methyl 2-methylfuran-3-carboxylate | iPr | Me | Me | O | S |
| 153 | methyl 2-methylfuran-3-carboxylate | Et | Me | Me | O | O |
| 154 | methyl 2-methylfuran-3-carboxylate | iPr | Me | Me | O | O |
| 155 | methyl 2-methylfuran-3-carboxylate | Et | Me | Me | O | C=O |
| 156 | methyl 2-methylfuran-3-carboxylate | iPr | Me | Me | O | C=O |
| 157 | acetyl | Et | Me | Me | O | O |
| 158 | acetyl | iPr | Me | Me | O | O |
| 159 | acetyl | Et | Me | Me | O | C=O |
| 160 | acetyl | iPr | Me | Me | O | C=O |

-continued

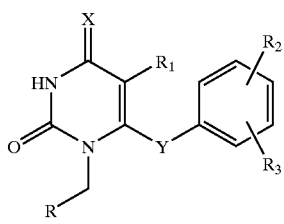

(I)

| No. of Example | R | R₁ | R₂ | R₃ | X | Y |
|---|---|---|---|---|---|---|
| 161 | H₃C-CH(-)-C(=O)- | Et | Me | Me | O | O |
| 162 | H₃C-CH(-)-C(=O)- | iPr | Me | Me | O | O |
| 163 | H₃C-CH(-)-C(=O)- | Et | Me | Me | O | C=O |
| 164 | H₃C-CH(-)-C(=O)- | iPr | Me | Me | O | C=O |
| 165 | Ph-CH(-)-C(=O)- | Et | Me | Me | O | O |
| 166 | Ph-CH(-)-C(=O)- | iPr | Me | Me | O | O |
| 167 | Ph-CH(-)-C(=O)- | Et | Me | Me | O | C=O |
| 168 | Ph-CH(-)-C(=O)- | iPr | Me | Me | O | C=O |

Example 1

1-(Cyclopropyl)methyl-5-ethyl-6-(3,5-dimethylphenyl)thio-2,4-pyrimidinedione

To a solution of 5-ethyl-6-(3,5-dimethylphenyl)thio-2,4-pyrimidinedione 276 mg, 1.0 mmol) and bromomethyl cyclopropane (160 mg, 1.0 mmol, 85%) dissolved in dimethylformamide (5 ml), sodium bicarbonate (126 mg, 1.50 mmol) and lithium iodide (13.0 mg, 0.10 mmol) were added. The resulting mixture was stirred at 90° C. for 24 hrs, distilled under the reduced pressure to remove dimethylformamide and purified with column chromatography to obtain the titled compound as a white solid (152 mg, yield: 46.0%).

Example 2

1-(Cyclopropyl)methyl-5-isopropyl-6-(3,5-dimethylphenyl)thio-2,4-pyrimidinedione 5-Isopropyl-6-(3,5-dimethylphenyl)thio-2,4-pyrimidinedione and bromomethyl cyclopropane were reacted by the same way with the example 1 to obtain the titled compound (170 mg, yield: 49.4%).

Example 3

1-(Cyclopropyl)methyl-5-ethyl-6-(3,5-dimethylphenoxy)-2,4-pyrimidinedione

5-Ethyl-6-(3,5-dimethylphenoxy)-2,4-pyrimidinedione and bromomethyl cyclopropane were reacted by the same way with the example 1 to obtain the titled compound (146 mg, yield: 46.4%).

Example 4

1-(Cyclopropyl)methyl-5-isopropyl-6-(3,5-dimethylphenoxy)-2,4-pyrimidinedione

5-Isopropyl-6-(3,5-dimethylphenoxy)-2,4-pyrimidinedione and bromomethyl cyclopropane were reacted by the same way with the example 1 to obtain the titled compound (132 mg, yield: 40.2%).

Example 5

1-(Cyclopropyl)methyl-5-ethyl-6-(3,5-dimethylbenzoyl)-2,4-pyrimidinedione

5-Ethyl-6-(3,5-dimethylbenzoyl)-2,4-pyrimidinedione and bromomethyl cyclopropane were reacted by the same way with the example 1 to obtain the titled compound (165 mg, yield: 50.6%).

Example 6

1-(Cyclopropyl)methyl-5-isopropyl-6-(3,5-dimethylbenzoyl)-2,4-pyrimidinedione

5-Isopropyl-6-(3,5-dimethylbenzoyl)-2,4-pyrimidinedione and bromomethyl cyclopropane were reacted by the same way with the example 1 to obtain the titled compound (158 mg, yield: 46.4%).

Example 7

1-(Cyclobutyl)methyl-5-ethyl-6-(3,5-dimethylphenyl)thio-2,4-pyrimidinedione

5-Ethyl-6-(3,5-dimethylphenyl)thio-2,4-pyrimidinedione and (cyclobutyl) methyl para-toluenesulfonate were reacted by the same way with the example 1 to obtain the titled compound (150 mg, yield: 43.5%).

Example 8

1-(Cyclobutyl)methyl-5-isopropyl-6-(3,5-dimethylphenyl)thio-2,4-pyrimidinedione

5-Isopropyl-6-(3,5-dimethylphenyl)thio-2,4-pyrimidinedione and (cyclobutyl)methyl para-toluenesulfonate were reacted by the same way with the example 1 to obtain the titled compound (147 mg, yield: 41.0%).

Example 9

1-(Cyclobutyl)methyl-5-ethyl-6-(3,5-dimethylphenoxy)-2,4-pyrimidinedione

5-Ethyl-6-(3,5-dimethylphenoxy)-2,4-pyrimidinedione and (cyclobutyl)methyl para-toluenesulfonate were reacted by the same way with the example 1 to obtain the titled compound (192 mg, yield: 58.5%).

Example 10

1-(Cyclobutyl)methyl-5-isopropyl-6-(3,5-dimethylphenoxy)-2,4-pyrimidinedione

5-Isopropyl-6-(3,5-dimethylphenoxy)-2,4-pyrimidinedione and (cyclobutyl)methyl para-toluenesulfonate were reacted by the same way with the example 1 to obtain the titled compound (164 mg, yield: 47.9%).

Example 11

1-(Cyclobutyl)methyl-5-ethyl-6-(3,5-dimethylbenzoyl)-2,4-pyrimidinedione

5-Ehtyl-6-(3,5-dimethylbenzoyl)-2,4-pyrimidinedione and (cyclobutyl)methyl para-toluenesulfonate were reacted by the same way with the example 1 to obtain the titled compound (179 mg, yield: 52.6%).

Example 12

1-(Cyclobutyl)methyl-5-isopropyl-6-(3,5-dimethylbenzoyl)-2,4-pyrimidinedione

5-Isopropyl-6-(3,5-dimethylbenzoyl)-2,4-pyrimidinedione and (cyclobutyl)methyl para-toluenesulfonate were reacted by the same way ith the example 1 to obtain the titled compound (182 mg, yield: 1.3%).

Example 13

1-(Cyclohexyl)methyl-5-ethyl-6-(3,5-dimethylphenyl)thio-2,4-pyrimidinedione

5-Ethyl-6-(3,5-dimethylphenyl)thio-2,4-pyrimidinedione and (cyclohexyl)methyl para-toluenesulfonate were reacted by the same way with the example 1 to obtain the titled compound (195 mg, yield: 52.3%).

Example 14

1-(Cyclohexyl)methyl-5-isopropyl-6-(3,5-dimethylphenyl)thio-2,4-pyrimidinedione

5-Isopropyl-6-(3,5-dimethylphenyl)thio-2,4-pyrimidinedione and (cyclohexyl)methyl para-toluenesulfonate were reacted by the same way with the example 1 to obtain the titled compound (210 mg, yield: 54.3%).

Example 15

1-(Cyclohexyl)methyl-5-ethyl-6-(3,5-dimethylphenoxy)-2,4-pyrimidinedione

5-Ethyl-6-(3,5-dimethylphenoxy)-2,4-pyrimidinedione and (cyclohexyl)methyl para-toluenesulfonate were reacted by the same way with the example 1 to obtain the titled compound (185 mg, yield: 51.9%).

Example 16

1-(Cyclohexyl)methyl-5-isopropyl-6-(3,5-dimethylphenoxy)-2,4-pyrimidinedione

5-Isopropyl-6-(3,5-dimethylphenoxy)-2,4-pyrimidinedione and (cyclohexyl)methyl para-toluenesulfonate were reacted by the same way with the example 1 to obtain the titled compound (201 mg, yield: 54.3%).

Example 17

1-(Cyclohexyl)methyl-5-ethyl-6-(3,5-dimethylbenzoyl)-2,4-pyrimidinedione

5-Ethyl-6-(3,5-dimethylbenzoyl)-2,4-pyrimidinedione and (cyclohexyl)methyl para-toluenesulfonate were reacted by the same way with the example 1 to obtain the titled compound (233 mg, yield: 63.2%).

Example 18

1-(Cyclohexyl)methyl-5-isopropyl-6-(3,5-dimethylbenzoyl)-2,4-pyrimidinedione

5-Isopropyl-6-(3,5-dimethylbenzoyl)-2,4-pyrimidinedione and (cyclohexyl)methyl para-toluenesulfonate were reacted by the same way with the example 1 to obtain the titled compound (212 mg, yield: 55.4%).

Example 19

1-Benzyl-5-ethyl-6-(3,5-dimethylphenyl)thio-2,4-pyrimidine-dione

5-Ethyl-6-(3,5-dimethylphenyl)thio-2,4-pyrimidinedione and benzyl bromide were reacted by the same way with the example 1 to obtain the titled compound (275 mg, yield: 75.0%).

Example 20

1-Benzyl-5-isopropyl-6-(3,5-dimethylphenyl)thio-2,4-pyrimidinedione

5-Isopropyl-6-(3,5-dimethylphenyl)thio-2,4-pyrimidinedione and benzyl bromide were reacted by the same way with the example 1 to obtain the titled compound (300 mg, yield: 79.0%).

Example 21

1-Benzyl-5-ethyl-6-(3,5-dimethylphenoxy)-2,4-pyrimidine-dione

5-Ethyl-6-(3,5-dimethylphenoxy)-2,4-pyrimidinedione and benzyl bromide were reacted by the same way with the example 1 to obtain the titled compound (285 mg, yield: 72.5%).

Example 22

1-Benzyl-5-isopropyl-6-(3,5-dimethylphenoxy)-2,4-pyrimidinedione

5-Isopropyl-6-(3,5-dimethylphenoxy)-2,4-pyrimidinedione and benzyl bromide were reacted by the same way with the example 1 to obtain the titled compound (264 mg, yield: 72.5%).

Example 23

1-Benzyl-5-ethyl-6-(3,5-dimethylbenzoyl)-2,4-pyrimidine-dione

5-Ethyl-6-(3,5-dimethylbenzoyl)-2,4-pyrimidinedione and benzyl bromide were reacted by the same way with the example 1 to obtain the titled compound (289 mg, yield: 79.8%).

Example 24

1-Benzyl-5-isopropyl-6-(3,5-dimethylbenzoyl)-2,4-pyrimidinedione

5-Isopropyl-6-(3,5-dimethylbenzoyl)-2,4-pyrimidinedione and benzyl bromide were reacted by the same way with the example 1 to obtain the titled compound (293 mg, yield: 78.0%).

Example 25

1-(3-Methoxybenzyl)-5-ethyl-6-(3,5-dimethylphenyl)thio-2,4-pyrimidinedione

5-Ethyl-6-(3,5-dimethylphenyl)thio-2,4-pyrimidinedione and 3-methoxylbenzyl bromide were reacted by the same way with the example 1 to obtain the titled compound (175 mg, yield: 44.1%).

Example 26

1-(3-Methoxybenzyl)-5-isopropyl-6-(3,5-dimethylphenyl)thio-2,4-pyrimidinedione

5-Isopropyl-6-(3,5-dimethylphenyl)thio-2,4-pyrimidinedione and 3-methoxybenzyl bromide were reacted by the same way with the example 1 to obtain the titled compound (203 mg, yield: 49.4%).

Example 27

1-(3-Methoxybenzyl)-5-ethyl-6-(3,5-dimethylphenoxy)-2,4-pyrimidinedione

5-Ethyl-6-(3,5-dimethylphenoxy)-2,4-pyrimidinedione and 3-methoxybenzyl bromide were reacted by the same way with the example 1 to obtain the titled compound (213 mg, yield: 56.0%).

Example 28

1-(3-Methoxybenzyl)-5-isopropyl-6-(3,5-dimethylphenoxy)-2,4-pyrimidinedione

5-Isopropyl-6-(3,5-dimethylphenoxy)-2,4-pyrimidinedione and 3-methoxybenzyl bromide were reacted by the same way with the example 1 to obtain the titled compound (217 mg, yield: 55.0%).

Example 29

1-(3-Methoxybenzyl)-5-ethyl-6-(3,5-dimethylbenzoyl)-2,4-pyrimidinedione

5-Ethyl-6-(3,5-dimethylbenzoyl)-2,4-pyrimidinedione and 3-methoxybenzyl bromide were reacted by the same way with the example 1 to obtain the titled compound (252 mg, yield: 64.2%).

Example 30

1-(3-Methoxybenzyl)-5-isopropyl-6-(3,5-dimethylbenzoyl)-2,4-pyrimidinedione

5-Isopropyl-6-(3,5-dimethylbenzoyl)-2,4-pyrimidinedione and 3-methpoxybenzyl bromide were reacted by the same way with the example 1 to obtain the titled compound (235 mg, yield: 57.8%).

Example 31

1-(4-Trifluoromethoxybenzyl)-5-ethyl-6-(3,5-dimethylphenyl)thio-2,4-pyrimidinedione 5-Ethyl-6-(3,5-dimethylphenyl)thio-2,4-pyrimidinedione and 4-trifluoro-methoxybenzyl bromide were reacted by the same way with the example 1 to obtain the titled compound (195 mg, yield: 43.3%).

Example 32

1-(4-Trifluoromethoxybenzyl)-5-isopropyl-6-(3,5-dimethylphenyl)thio-2,4-pyrimidinedione 5-Isopropyl-6-(3,5-dimethylphenyl)thio-2,4-pyrimidinedione and 4-trifluoromethoxybenzyl bromide were reacted by the same way with the example 1 to obtain the titled compound (208 mg, yield: 44.8%).

Example 33

1-(4-Trifluoromethoxybenzyl)-5-ethyl-6-(3,5-dimethyl-phenoxy)-2,4-pyrimidinedione 5-Ethyl-6-(3,5-dimethylphenoxy)-2,4-pyrimidinedione and 4-trifluoromethoxybenzyl bromide were reacted by the same way with the example 1 to obtain the titled compound (233 mg, yield: 53.6%).

Example 34

1-(4-Trifluoromethoxybenzyl)-5-isopropyl-6-(3,5-dimethylphenoxy)-2,4-pyrimidinedione 5-Isopropyl-6-(3,5-dimethylphenoxy)-2,4-pyrimidinedione and 4-trifluoromethoxybenzyl bromide were reacted by the same way with the example 1 to obtain the titled compound (212 mg, yield: 47.3%).

Example 35

1-(4-Trifluoromethoxybenzyl)-5-ethyl-6-(3,5-dimethylbenzoyl)-2,4-pyrimidinedione 5-Ethyl-6-(3,5-dimethylbenzoyl)-2,4-pyrimidinedione and 4-trifluoromethoxybenzyl bromide were reacted by the same way with the example 1 to obtain the titled compound (285 mg, yield: 63.8%).

Example 36

1-(4-Trifluoromethoxybenzyl)-5-isopropyl-6-(3,5-dimethyl-benzoyl)-2,4-pyrimidinedione 5-Isopropyl-6-(3,5-dimethylbenzoyl)-2,4-pyrimidinedione and 4-trifluoromethoxybenzyl bromide were reacted by the same way with the example 1 to obtain the titled compound (304 mg, yield: 66.0%).

Example 37

1-(2-Cyanobenzyl)-5-ethyl-6-(3,5-dimethylphenyl)thio-2,4-pyrimidinedione

5-Ethyl-6-(3,5-dimethylphenyl)thio-2,4-pyrimidinedione and 2-cyanobenzyl bromide were reacted by the same way with the example 1 to obtain the titled compound (162 mg, yield: 41.3%).

Example 38

1-(2-Cyanobenzyl)-5-isopropyl-6-(3,5-dimethylphenyl)-thio- 2,4-pyrimidinedione

5-Isopropyl-6-(3,5-dimethylphenyl)thio-2,4-pyrimidinedione and 2-cyanobenzyl bromide were reacted by the same way with the example 1 to obtain the titled compound (188 mg, yield: 46.4%).

Example 39

1-(2-Cyanobenzyl)-5-ethyl-6-(3,5-dimethylphenoxy)-2,4-pyrimidinedione

5-Ethyl-6-(3,5-dimethylphenoxy)-2,4-pyrimidinedione and 2-cyanobenzyl bromide were reacted by the same way with the example 1 to obtain the titled compound (201 mg, yield: 53.5%).

Example 40

1-(2-Cyanobenzyl)-5-isopropyl-6-(3,5-dimethylphenoxy)-2,4-pyrimidinedione

5-Isopropyl-6-(3,5-dimethylphenoxy)-2,4-pyrimidinedione and 2-cyanobenzyl bromide were reacted by the same way with the example 1 to obtain the titled compound (154 mg, yield: 39.5%).

Example 41

1-(2-Cyanobenzyl)-5-ethyl-6-(3,5-dimethylbenzoyl)-2,4-pyrimidinedione

5-Ethyl-6-(3,5-dimethylbenzoyl)-2,4-pyrimidinedione and 2-cyanobenzyl bromide were reacted by the same way with the example 1 to obtain the titled compound (199 mg, yield: 51.4%).

Example 42

1-(2-Cyanobenzyl)-5-isopropyl-6-(3,5-dimethylbenzoyl)-2,4-pyrimidinedione

5-Isopropyl-6-(3,5-dimethylbenzoyl)-2,4-pyrimidinedione and 2-cyanobenzyl bromide were reacted by the same way with the example 1 to obtain the titled compound (231 mg, yield: 57.5%).

Example 43

1-(3-Cyanobenzyl)-5-ethyl-6-(3,5-dimethylphenyl)thio-2,4-pyrimidinedione

5-Ethyl-6-(3,5-dimethylphenyl)thio-2,4-pyrimidinedione and 3-cyanobenzyl bromide were reacted by the same way with the example 1 to obtain the titled compound (185 mg, yield: 47.3%).

Example 44

1-(3-Cyanobenzyl)-5-isopropyl-6-(3,5-dimethylphenyl)thio-2,4-pyrimidinedione

5-Isopropyl-6-(3,5-dimethylphenyl)thio-2,4-pyrimidinedione and 3-cyanobenzyl bromide were reacted by the same way with the example 1 to obtain the titled compound (176 mg, yield: 43.4%).

Example 45

1-(3-Cyanobenzyl)-5-ethyl-6-(3,5-dimethylphenoxy)-2,4-pyrimidinedione

5-Ethyl-6-(3,5-dimethylphenoxy)-2,4-pyrimidinedione and 3-cyanobenzyl bromide were reacted by the same way with the example 1 to obtain the titled compound (216 mg, yield: 57.5%).

Example 46

1-(3-Cyanobenzyl)-5-isopropyl-6-(3,5-dimethylphenoxy)-2,4-pyrimidinedione

5-Isopropyl-6-(3,5-dimethylphenoxy)-2,4-pyrimidinedione and 3-cyanobenzyl bromide were reacted by the same way with the example 1 to obtain the titled compound (193 mg, yield: 49.6%).

Example 47

1-(3-Cyanobenzyl)-5-ethyl-6-(3,5-dimethylbenzoyl)-2,4-pyrimidinedione

5-Ethyl-6-(3,5-dimethylbenzoyl)-2,4-pyrimidinedione and 3-cyanobenzyl bromide were reacted by the same way with the example 1 to obtain the titled compound (207 mg, yield: 53.4%).

Example 48

1-(3-Cyanobenzyl)-5-isopropyl-6-(3,5-dimethylbenzoyl)-2,4-pyrimidinedione

5-Isopropyl-6-(3,5-dimethylbenzoyl)-2,4-pyrimidinedione and 3-cyanobenzyl bromide were reacted by the same way with the example 1 to obtain the titled compound (222 mg, yield: 55.3%).

Example 49

1-(3,5-Dimethylbenzyl)-5-ethyl-6-(3,5-dimethylphenyl)thio-2,4-pyrimidinedione

5-Ethyl-6-(3,5-dimethylphenyl)thio-2,4-pyrimidinedione and 3,5-dimethylbenzyl bromide were reacted by the same way with the example 1 to obtain the titled compound (265 mg, yield: 67.2%).

Example 50

1-(3,5-Dimethylbenzyl)-5-isopropyl-6-(3,5-dimethylphenyl)thio-2,4-pyrimidinedione 5-Isopropyl-6-(3,5-dimethylphenyl)thio-2,4-pyrimidinedione and 3,5-dimethylbenzyl bromide were reacted by the same way with the example 1 to obtain the titled compound (230 mg, yield: 56.3%).

Example 51

1-(3,5-Dimethylbenzyl)-5-ethyl-6-(3,5-dimethylphenoxy)-2,4-pyrimidinedione

5-Ethyl-6-(3,5-dimethylphenoxy)-2,4-pyrimidinedione and 3,5-dimethylbenzyl bromide were reacted by the same way with the example 1 to obtain the titled compound (217 mg, yield: 57.3%).

Example 52

1-(3,5-Dimethylbenzyl)-5-isopropyl-6-(3,5-dimethyl-phenoxy)-2,4-pyrimidinedione

5-Isopropyl-6-(3,5-dimethylphenoxy)-2,4-pyrimidinedione and 3,5-dimethylbenzyl bromide were reacted by the same way with the example 1 to obtain the titled compound (260 mg, yield: 66.2%).

Example 53

1-(3,5-Dimethylbenzyl)-5-ethyl-6-(3,5-dimethylbenzoyl)-2,4-pyrimidinedione

5-Ethyl-6-(3,5-dimethylbenzoyl)-2,4-pyrimidinedione and 3,5-dimethylbenzyl bromide were reacted by the same way with the example 1 to obtain the titled compound (288 mg, yield: 73.8%).

Example 54

1-(3,5-Dimethylbenzyl)-5-isopropyl-6-(3,5-dimethylbenzoyl)-2,4-pyrimidinedione

5-Isopropyl-6-(3,5-dimethylbenzoyl)-2,4-pyrimidinedione and 3,5-dimethylbenzyl bromide were reacted by the same way with the example 1 to obtain the titled compound (322 mg, yield: 79.5%).

Example 55

1-(3,5-Dimethoxybenzyl)-5-ethyl-6-(3,5-dimethylphenyl)thio-2,4-pyrimidinedione

5-Ethyl-6-(3,5-dimethylphenyl)thio-2,4-pyrimidinedione and 3,5-dimethoxybenzyl bromide were reacted by the same way with the example 1 to obtain the titled compound (252 mg, yield: 59.1%).

Example 56

1-(3,5-Dimethoxybenzyl)-5-isopropyl-6-(3,5-dimethyl-phenyl)thio-2,4-pyrimidinedione 5-Isopropyl-6-(3,5-dimethylphenyl)thio-2,4-pyrimidinedione and 3,5-dimethoxybenzyl bromide were reacted by the same way with the example 1 to obtain the titled compound (234 mg, yield: 53.1%).

Example 57

1-(3,5-Dimethoxybenzyl)-5-ethyl-6-(3,5-dimethylphenoxy)-2,4-pyrimidinedione

5-Ethyl-6-(3,5-dimethylphenoxy)-2,4-pyrimidinedione and 3,5-dimethoxybenzyl bromide were reacted by the same way with the example 1 to obtain the titled compound (279 mg, yield: 68.0%).

Example 58

1-(3,5-Dimethoxybenzyl)-5-isopropyl-6-(3,5-dimethylphenoxy)-2,4-pyrimidinedione

5-Isopropyl-6-(3,5-dimethylphenoxy)-2,4-pyrimidinedione and 3,5-dimethoxybenzyl bromide were reacted by the same way with the example 1 to obtain the titled compound (275 mg, yield: 64.8%).

Example 59

1-(3,5-Dimethoxybenzyl)-5-ethyl-6-(3,5-dimethylbenzoyl)-2,4-pyrimidinedione

5-Ethyl-6-(3,5-dimethylbenzoyl)-2,4-pyrimidinedione and 3,5-dimethoxybenzyl bromide were reacted by the same way with the example 1 to obtain the titled compound (212 mg, yield: 50.2%).

Example 60

1-(3,5-Dimethoxybenzyl)-5-isopropyl-6-(3,5-dimethyl-benzoyl)-2,4-pyrimidinedione 5-Isopropyl-6-(3,5-dimethylbenzoyl)-2,4-pyrimidinedione and 3,5-dimethoxybenzyl bromide were reacted by the same way with the example 1 to obtain the titled compound (296 mg, yield: 67.8%).

Example 61

1-[3,5-Bis(trifluoromethyl)benzyl]-5-ethyl-6-(3,5-dimethyl-phenyl)thio-2,4-pyrimidinedione 5-Ethyl-6-(3,5-dimethylphenyl)thio-2,4-pyrimidinedione and 3,5-bis(trifluoromethyl)benzyl bromide were reacted by the same way with the example 1 to obtain the titled compound (226 mg, yield: 45.0%).

Example 62

1-[3,5-Bis(trifluoromethyl)benzyl]-5-isopropyl-6-(3,5-dimethylphenyl)thio-2,4-pyrimidinedione 5-Isopropyl-6-(3,5-dimethylphenyl)thio-2,4-pyrimidinedione and 3,5-bis(trifluoromethyl)benzyl bromide were reacted by the same way with the example 1 to obtain the titled compound (195 mg, yield: 37.8%).

Example 63

1-[3,5-Bis(Trifluoromethyl)benzyl]-5-ethyl-6-(3,5-dimethyl-phenoxy)-2,4-pyrimidinedione 5-Ethyl-6-(3,5-dimethylphenoxy)-2,4-pyrimidinedione and 3,5-bis(trifluoromethyl)benzyl bromide were reacted by the same way with the example 1 to obtain the titled compound (240 mg, yield: 49.4%).

Example 64

1-[3,5-Bis(Trifluoromethyl)benzyl]-5-isopropyl-6-(3,5-dimethylphenoxy)-2,4-pyrimidinedione 5-Isopropyl-6-(3,5-dimethylphenoxy)-2,4-pyrimidinedione and 3,5-bis(trifluoromethyl)benzyl bromide were reacted by the same way with the example 1 to obtain the titled compound (266 mg, yield: 53.2%).

Example 65

1-[3,5-Bis(Trifluoromethyl)benzyl]-5-ethyl-6-(3,5-dimethyl-benzoyl)-2,4-pyrimidinedione 5-Ethyl-6-(3,5-dimethylbenzoyl)-2,4-pyrimidinedione and 3,5-bis(trifluoromethyl)benzyl bromide were reacted by the same way with the example 1 to obtain the titled compound (280 mg, yield: 56.2%).

Example 66

1-[3,5-Bis(Trifluoromethyl)benzyl]-5-isopropyl-6-(3,5-dimethyl-benzoyl)-2,4-pyrimidinedione 5-Isopropyl-6-(3,5-dimethylbenzoyl)-2,4-pyrimidinedione and 3,5-bis(trifluoromethyl)benzyl bromide were reacted by the same way with the example 1 to obtain the titled compound (255 mg, yield: 49.8%).

Example 67

1-(2,5-Difluorobenzyl)-5-ethyl-6-(3,5-dimethylphenyl)thio-2,4-pyrimidinedione

5-Ethyl-6-(3,5-dimethylphenyl)thio-2,4-pyrimidinedione and 2,5-difluorobenzyl bromide were reacted by the same way with the example 1 to obtain the titled compound (170 mg, yield: 42.2%).

Example 68

1-(2,5-Difluorobenzyl)-5-isopropyl-6-(3,5-dimethylphenyl)thio-2,4-pyrimidinedione 5-Isopropyl-6-(3,5-dimethylphenyl)thio-2,4-pyrimidinedione and 2,5-difluorobenzyl bromide were reacted by the same way with the example 1 to obtain the titled compound (205 mg, yield: 49.2%).

Example 69

1-(2,5-Difluorobenzyl)-5-ethyl-6-(3,5-dimethylphenoxy)-2,4-pyrimidinedione

5-Ethyl-6-(3,5-dimethylphenoxy)-2,4-pyrimidinedione and 2,5-difluorobenzyl bromide were reacted by the same way with the example 1 to obtain the titled compound (185 mg, yield: 47.9%).

Example 70

1-(2,5-Difluorobenzyl)-5-isopropyl-6-(3,5-dimethylphenoxy)-2,4-pyrimidinedione

5-Isopropyl-6-(3,5-dimethylphenoxy)-2,4-pyrimidinedione and 2,5-difluorobenzyl bromide were reacted by the same way with the example 1 to obtain the titled compound (165 mg, yield: 41.2%).

Example 71

1-(2,5-Difluorobenzyl)-5-ethyl-6-(3,5-dimethylbenzoyl)-2,4-pyrimidinedione

5-Ethyl-6-(3,5-dimethylbenzoyl)-2,4-pyrimidinedione and 2,5-difluorobenzyl bromide were reacted by the same way with the example 1 to obtain the titled compound (214 mg, yield: 53.7%).

Example 72

1-(2,5-Difluorobenzyl)-5-isopropyl-6-(3,5-dimethylbenzoyl)-2,4-pyrimidinedione

5-Isopropyl-6-(3,5-dimethylbenzoyl)-2,4-pyrimidinedione and 2,5-difluorobenzyl bromide were reacted by the same way with the example 1 to obtain the titled compound (200 mg, yield: 48.5%).

Example 73

1-(3,5-Difluorobenzyl)-5-ethyl-6-(3,5-dimethylphenyl)thio-2,4-pyrimidinedione

5-Ethyl-6-(3,5-dimethylphenyl)thio-2,4-pyrimidinedione and 3,5-difluorobenzyl bromide were reacted by the same way with the example 1 to obtain the titled compound (196 mg, yield: 48.7%).

Example 74

1-(3,5-Difluorobenzyl)-5-isopropyl-6-(3,5-dimethylphenyl)thio-2,4-pyrimidinedione 5-Isopropyl-6-(3,5-dimethylphenyl)thio-2,4-pyrimidinedione and 3,5-difluorobenzyl bromide were reacted by the same way with the example 1 to obtain the titled compound (205 mg, yield: 49.2%).

Example 75

1-(3,5-Difluorobenzyl)-5-ethyl-6-(3,5-dimethylphenoxy)-2,4-pyrimidinedione

5-Ethyl-6-(3,5-dimethylphenoxy)-2,4-pyrimidinedione and 3,5-difluorobenzyl bromide were reacted by the same way with the example 1 to obtain the titled compound (195 mg, yield: 50.5%).

Example 76

1-(3,5-Difluorobenzyl)-5-isopropyl-6-(3,5-dimethylphenoxy)-2,4-pyrimidinedione

5-Isopropyl-6-(3,5-dimethylphenoxy)-2,4-pyrimidinedione and 3,5-difluorobenzyl bromide were reacted by the same way with the example 1 to obtain the titled compound (180 mg, yield: 45.0%).

Example 77

1-(3,5-Difluorobenzyl)-5-ethyl-6-(3,5-dimethylbenzoyl)-2,4-pyrimidinedione

5-Ethyl-6-(3,5-dimethylbenzoyl)-2,4-pyrimidinedione and 3,5-difluorobenzyl bromide were reacted by the same way with the example 1 to obtain the titled compound (236 mg, yield: 59.2%).

Example 78

1-(3,5-Difluorobenzyl)-5-isopropyl-6-(3,5-dimethylbenzoyl)-2,4-pyrimidinedione

5-Isopropyl-6-(3,5-dimethylbenzoyl)-2,4-pyrimidinedione and 3,5-difluorobenzyl bromide were reacted by the same way with the example 1 to obtain the titled compound (220 mg, yield: 53.3%).

Example 79

1-(3,5-Dichlorobenzyl)-5-ethyl-6-(3,5-dimethylphenyl)thio-2,4-pyrimidinedione

5-Ethyl-6-(3,5-dimethylphenyl)thio-2,4-pyrimidinedione and 3,5-dichlorobenzyl bromide were reacted by the same way with the example 1 to obtain the titled compound (292 mg, yield: 67.1%).

Example 80

1-(3,5-Dichlorobenzyl)-5-isopropyl-6-(3,5-dimethylphenyl)thio-2,4-pyrimidinedione 5-isopropyl-6-(3,5-dimethylphenyl)thio-2,4-pyrimidinedione and 3,5-dichlorobenzyl bromide were reacted by the same way with the example 1 to obtain the titled compound (250 mg, yield: 55.6%).

Example 81

1-(3,5-Dichlorobenzyl)-5-ethyl-6-(3,5-dimethylphenoxy)-2,4-pyrimidinedione

5-Ethyl-6-(3,5-dimethylphenoxy)-2,4-pyrimidinedione and 3,5-dichlorobenzyl bromide were reacted by the same way with the example 1 to obtain the titled compound (220 mg, yield: 52.7%).

Example 82

1-(3,5-Dichlorobenzyl)-5-isopropyl-6-(3,5-dimethylphenoxy)-2,4-pyrimidinedione 5-isopropyl-6-(3,5-dimethylphenoxy)-2,4-pyrimidinedione and 3,5-dichlorobenzyl bromide were reacted by the same way with the example 1 to obtain the titled compound (235 mg, yield: 54.2%).

Example 83

1-(3,5-Dichlorobenzyl)-5-ethyl-6-(3,5-dimethylbenzoyl)-2,4-pyrimidinedione

5-Ethyl-6-(3,5-dimethylbenzol)-2,4-pyrimidinedione and 3,5-dichlorobenzyl bromide were reacted by the same way with the example 1 to obtain the titled compound (287 mg, yield: 66.5%).

Example 84

1-(3,5-Dichlorobenzyl)-5-isopropyl-6-(3,5-dimethylbenzoyl)-2,4-pyrimidinedione 5-isopropyl-6-(3,5-dimethylbenzoyl)-2,4-pyrimidinedione and 3,5-dichlorobenzyl bromide were reacted by the same way with the example 1 to obtain the titled compound (283 mg, yield: 63.6%).

Example 85

1-(3,5-Dibromobenzyl)-5-ethyl-6-(3,5-dimethylphenyl)thio-2,4-pyrimidinedione

5-Ethyl-6-(3,5-dimethylphenyl)thio-2,4-pyrimidinedione and 3,5-dibromobenzyl bromide were reacted by the same way with the example 1 to obtain the titled compound (356 mg, yield: 67.9%).

Example 86

1-(3,5-Dibromobenzyl)-5-isopropyl-6-(3,5-dimethylphenyl)thio-2,4-pyrimidinedione 5-Isopropyl-6-(3,5-dimethylphenyl)thio-2,4-pyrimidinedione and 3,5-dibromobenzyl bromide were reacted by the same way with the example 1 to obtain the titled compound (380 mg, yield: 70.6%).

Example 87

1-(3,5-Dibromobenzyl)-5-ethyl-6-(3,5-dimethylphenoxy)-2,4-pyrimidinedione

5-Ethyl-6-(3,5-dimethylphenoxy)-2,4-pyrimidinedione and 3,5-dibromobenzyl bromide were reacted by the same way with the example 1 to obtain the titled compound (375 mg, yield: 73.9%).

Example 88

1-(3,5-Dibromobenzyl)-5-isopropyl-6-(3,5-dimethylphenoxy)-2,4-pyrimidinedione

5-Isopropyl-6-(3,5-dimethylphenoxy)-2,4-pyrimidinedione and 3,5-dibromobenzyl bromide were reacted by the same way with the example 1 to obtain the titled compound (395 mg, yield: 75.6%).

Example 89

1-(3,5-Dibromobenzyl)-5-ethyl-6-(3,5-dimethylbenzoyl)-2,4-pyrimidinedione

5-Ethyl-6-(3,5-dimethylbenzoyl)-2,4-pyrimidinedione and 3,5-dibromobenzyl bromide were reacted by the same way with the example 1 to obtain the titled compound (387 mg, yield: 74.4%).

Example 90

1-(3,5-Dibromobenzyl)-5-isopropyl-6-(3,5-dimethylbenzoyl)-2,4-pyrimidinedione

5-Isopropyl-6-(3,5-dimethylbenzoyl)-2,4-pyrimidinedione and 3,5-dibromobenzyl bromide were reacted by the same way with the example 1 to obtain the titled compound (402 mg, yield: 75.2%).

Example 91

1-(2-Naphthalenemethyl)-5-ethyl-6-(3,5-dimethylphenyl)thio-2,4-pyrimidinedione

5-Ethyl-6-(3,5-dimethylphenyl)thio-2,4-pyrimidinedione and 2-bromomethyl naphthalene were reacted by the same way with the example 1 to obtain the titled compound (265 mg, yield: 63.6%).

Example 92

1-(2-Naphthalenemethyl)-5-isopropyl-6-(3,5-dimethyl-phenyl)thio-2,4-pyrimidinedione 5-Isopropyl-6-(3,5-dimethylphenyl)thio-2,4-pyrimidinedione and 2-bromomethyl naphthalene were reacted by the same way with the example 1 to obtain the titled compound (298 mg, yield: 69.2%).

Example 93

1-(2-Naphthalenemethyl)-5-ethyl-6-(3,5-dimethylphenoxy)-2,4-pyrimidinedione

5-Ethyl-6-(3,5-dimethylphenoxy)-2,4-pyrimidinedione and 2-bromomethyl naphthalene were reacted by the same way with the example 1 to obtain the titled compound (272 mg, yield: 67.9%).

Example 94

1-(2-Naphthalenemethyl)-5-isopropyl-6-(3,5-dimethylphenoxy)-2,4-pyrimidinedione

5-Isopropyl-6-(3,5-dimethylphenoxy)-2,4-pyrimidinedione and 2-bromomethyl naphthalene were reacted by the same way with the example 1 to obtain the titled compound (274 mg, yield: 66.1%).

Example 95

1-(2-Naphthalenemethyl)-5-ethyl-6-(3,5-dimethylbenzoyl)-2,4-pyrimidinedione

5-Ethyl-6-(3,5-dimethylbenzoyl)-2,4-pyrimidinedione and 2-bromomethyl naphthalene were reacted by the same way with the example 1 to obtain the titled compound (251 mg, yield: 60.9%).

Example 96

1-(2-Naphthalenemethyl)-5-isopropyl-6-(3,5-dimethyl-benzoyl)-2,4-pyrimidinedione 5-Isopropyl-6-(3,5-dimethylbenzoyl)-2,4-pyrimidinedione and 2-bromomethyl naphthalene were reacted by the same way with the example 1 to obtain the titled compound (274 mg, yield: 64.2%).

Example 97

1-(Anthracen-9-ylmethyl)-5-ethyl-6-(3,5-dimethylphenyl)thio-2,4-pyrimidinedione

5-Ethyl-6-(3,5-dimethylphenyl)thio-2,4-pyrimidinedione and 9-chloromethyl anthracene were reacted by the same way with the example 1 to obtain the titled compound (195 mg, yield: 41.8%).

Example 98

1-(Anthracen-9-ylmethyl)-5-isopropyl-6-(3,5-dimethylphenyl)thio-2,4-pyrimidinedione 5-Isopropyl-6-(3,5-dimethylphenyl)thio-2,4-pyrimidinedione and 9-chloromethyl anthracene were reacted by the same way with the example 1 to obtain the titled compound (215 mg, yield: 44.7%).

Example 99

1-(Anthracen-9-ylmethyl)-5-ethyl-6-(3,5-dimethylphenoxy)-2,4-pyrimidinedione

5-Ethyl-6-(3,5-dimethylphenoxy)-2,4-pyrimidinedione and 9-chloromethyl anthracene were reacted by the same way with the example 1 to obtain the titled compound (187 mg, yield: 41.5%).

Example 100

1-(Anthracen-9-ylmethyl)-5-isopropyl-6-(3,5-dimethyl-phenoxy)-2,4-pyrimidinedione 5-Isopropyl-6-(3,5-dimethylphenoxy)-2,4-pyrimidinedione and 9-chloromethyl anthracene were reacted by the same way with the example 1 to obtain the titled compound (205 mg, yield: 44.1%).

Example 101

1-(Anthracen-9-ylmethyl)-5-ethyl-6-(3,5-dimethylbenzoyl)-2,4-pyrimidinedione

5-Ethyl-6-(3,5-dimethylbenzoyl)-2,4-pyrimidinedione and 9-chloromethyl anthracene were reacted by the same way with the example 1 to obtain the titled compound (216 mg, yield: 46.7%).

Example 102

1-(Anthracen-9-ylmethyl)-5-isopropyl-6-(3,5-dimethyl-benzoyl)-2,4-pyrimidinedione 5-Isopropyl-6-(3,5-dimethylbenzoyl)-2,4-pyrimidinedione and 9-chloromethyl anthracene were reacted by the same way with the example 1 to obtain the titled compound (192 mg, yield: 40.3%).

Example 103

1-(Anthraquinon-2-ylmethyl)-5-ethyl-6-(3,5-dimethyl-phenyl)thio-2,4-pyrimidinedione 5-Ethyl-6-(3,5-dimethylphenyl)thio-2,4-pyrimidinedione and 2-chloromethyl anthraquinone were reacted by the same way with the example 1 to obtain the titled compound (175 mg, yield: 35.1%).

Example 104

1-(Anthraquinon-2-ylmethyl)-5-isopropyl-6-(3,5-dimethyl-phenyl)thio- 2,4-pyrimidinedione 5-Isopropyl-6-(3,5-dimethylphenyl)thio-2,4-pyrimidinedione and 2-chloromethyl anthraquinone were reacted by the same way with the example 1 to obtain the titled compound (165 mg, yield: 32.2%).

Example 105

1-(Anthraquinon-2-ylmethyl)-5-ethyl-6-(3,5-dimethylphenoxy)-2,4-pyrimidinedione

5-Ethyl-6-(3,5-dimethylphenoxy)-2,4-pyrimidinedione and 2-chloromethyl anthraquinone were reacted by the same way with the example 1 to obtain the titled compound (175 mg, yield: 36.3%).

Example 106

1-(Anthraquinon-2-ylmethyl)-5-isopropyl-6-(3,5-dimethylphenoxy)-2,4-pyrimidinedione 5-Isopropyl-6-(3,5-dimethylphenoxy)-2,4-pyrimidinedione and 2-chloromethyl anthraquinone were reacted by the same way with the example 1 to obtain the titled compound (155 mg, yield: 31.2%).

Example 107

1-(Anthraquinon-2-ylmethyl)-5-ethyl-6-(3,5-dimethylbenzoyl)-2,4-pyrimidinedione

5-Ethyl-6-(3,5-dimethylbenzoyl)-2,4-pyrimidinedione and 2-chloromethyl anthraquinone were reacted by the same way with the example 1 to obtain the titled compound (178 mg, yield: 36.0%).

Example 108

1-(Anthraquinon-2-ylmethyl)-5-isopropyl-6-(3,5-dimethylbenzoyl)-2,4-pyrimidinedione 5-Isopropyl-6-(3,5-dimethylbenzoyl)-2,4-pyrimidinedione and 2-chloromethyl anthraquinone were reacted by the same way with the example 1 to obtain the titled compound (193 mg, yield: 38.0%).

Example 109

1-(Pyridin-2-ylmethyl)-5-ethyl-6-(3,5-dimethylphenyl)thio-2,4-pyrimidinedione

5-Ethyl-6-(3,5-dimethylphenyl)thio-2,4-pyrimidinedione and 2-picolyl chloride were reacted by the same way with the example 1 to obtain the titled compound (98 mg, yield: 26.7%).

Example 110

1-(Pyridin-2-ylmethyl)-5-isopropyl-6-(3,5-dimethylphenyl)thio-2,4-pyrimidinedione 5-Isopropyl-6-(3,5-dimethylphenyl)thio-2,4-pyrimidinedione and 2-picolyl chloride were reacted by the same way with the example 1 to obtain the titled compound (112 mg, yield: 29.4%).

Example 111

1-(Pyridin-2-ylmethyl)-5-ethyl-6-(3,5-dimethylphenoxy)-2,4-pyrimidinedione

5-Ethyl-6-(3,5-dimethylphenoxy)-2,4-pyrimidinedione and 2-picolyl chloride were reacted by the same way with the example 1 to obtain the titled compound (125 mg, yield: 35.6%).

Example 112

1-(Pyridin-2-ylmethyl)-5-isopropyl-6-(3,5-dimethylphenoxy)-2,4-pyrimidinedione

5-Isopropyl-6-(3,5-dimethylphenoxy)-2,4-pyrimidinedione and 2-picolyl chloride were reacted by the same way with the example 1 to obtain the titled compound (136 mg, yield: 37.2%).

Example 113

1-(Pyridin-2-ylmethyl)-5-ethyl-6-(3,5-dimethylbenzoyl)-2,4-pyrimidinedione

5-Ethyl-6-(3,5-dimethylbenzoyl)-2,4-pyrimidinedione and 2-picolyl chloride were reacted by the same way with the example 1 to obtain the titled compound (145 mg, yield: 39.9%).

Example 114

1-(Pyridin-2-2-ylmethyl)-5-isopropyl-6-(3,5-dimethyl-benzoyl)-2,4-pyrimidinedione 5-Isopropyl-6-(3,5-dimethylbenzoyl)-2,4-pyrimidinedione and 2-picolyl chloride were reacted by the same way with the example 1 to obtain the titled compound (135 mg, yield: 35.8%).

Example 115

1-(Pyridin-3-ylmethyl)-5-ethyl-6-(3,5-dimethylphenyl)thio-2,4-pyrimidinedione

5-Ethyl-6-(3,5-dimethylphenyl)thio-2,4-pyrimidinedione and 3-picolyl chloride were reacted by the same way with the example 1 to obtain the titled compound (95 mg, yield: 25.9%).

Example 116

1-(Pyridin-3-ylmethyl)-5-isopropyl-6-(3,5-dimethylphenyl)thio-2,4-pyrimidinedione 5-Isopropyl-6-(3,5-dimethylphenyl)thio-2,4-pyrimidinedione and 3-picolyl chloride were reacted by the same way with the example 1 to obtain the titled compound (88 mg, yield: 23.1%).

Example 117

1-(Pyridin-3-ylmethyl)-5-ethyl-6-(3,5-dimethylphenoxy)-2,4-pyrimidinedione 5-ethyl-6-(3,5-dimethylphenoxy)-2,4-pyrimidinedione and 3-picolyl chloride were reacted by the same way with the example 1 to obtain the titled compound (101 mg, yield: 28.7%).

Example 118

1-(Pyridin-3-ylmethyl)-5-isopropyl-6-(3,5-dimethylphenoxy)-2,4-pyrimidinedione

5-Isopropyl-6-(3,5-dimethylphenoxy)-2,4-pyrimidinedione and 3-picolyl chloride were reacted by the same way with the example 1 to obtain the titled compound (122 mg, yield: 33.4%).

Example 119

1-(Pyridin-3-ylmethyl)-5-ethyl-6-(3,5-dimethylbenzoyl)-2,4-pyrimidinedione

5-Ethyl-6-(3,5-dimethylbenzoyl)-2,4-pyrimidinedione and 3-picolyl chloride were reacted by the same way with the example 1 to obtain the titled compound (120 mg, yield: 33.0%).

Example 120

1-(Pyridin-3-ylmethyl)-5-isopropyl-6-(3,5-dimethylbenzoyl)-2,4-pyrimidinedione

5-Isopropyl-6-(3,5-dimethylbenzoyl)-2,4-pyrimidinedione and 3-picolyl chloride were reacted by the same way with the example 1 to obtain the titled compound (152 mg, yield: 40.3%).

Example 121

1-(2-Chloropyridin-6-ylmethyl)-5-ethyl-6-(3,5-dimethyl-phenyl)thio-2,4-pyrimidinedione 5-Ethyl-6-(3,5-dimethylphenyl)thio-2,4-pyrimidinedione and 2-chloro-6-picolyl bromide were reacted by the same way with the example 1 to obtain the titled compound (122 mg, yield: 30.4%).

Example 122

1-(2-Chloropyridin-6-ylmethyl)-5-isopropyl-6-(3,5-dimethylphenyl)thio-2,4-pyrimidinedione 5-Isopropyl-6-(3,5-dimethylphenyl)thio-2,4-pyrimidinedione and 2-chloro-6-picolyl bromide were reacted by the same way with the example 1 to obtain the titled compound (130 mg, yield: 31.3%).

Example 123

1-(2-Chloropyridin-6-ylmethyl)-5-ethyl-6-(3,5-dimethylphenoxy)-2,4-pyrimidinedione 5-Ethyl-6-(3,5-dimethylphenoxy)-2,4-pyrimidinedione and 2-chloro-6-picolyl bromide were reacted by the same way with the example 1 to obtain the titled compound (126 mg, yield: 32.7%).

Example 124

1-(2-Chloropyridin-6-ylmethyl)-5-isopropyl-6-(3,5-dimethylphenoxy)-2,4-pyrimidinedione 5-Isopropyl-6-(3,5-dimethylphenoxy)-2,4-pyrimidinedione and 2-chloro-6-picolyl bromide were reacted by the same way with the example 1 to obtain the titled compound (135 mg, yield: 33.8%).

Example 125

1-(2-Chloropyridin-6-ylmethyl)-5-ethyl-6-(3,5-dimethyl-benzoyl)-2,4-pyrimidinedione 5-Ethyl-6-(3,5-dimethylbenzoyl)-2,4-pyrimidinedione and 2-chloro-6-picolyl bromide were reacted by the same way with the example 1 to obtain the titled compound (145 mg, yield: 36.4%).

Example 126

1-(2-Chloropyridin-6-ylmethyl)-5-isopropyl-6-(3,5-dimethylbenzoyl)-2,4-pyrimidinedione 5-Isopropyl-6-(3,5-dimethylbenzoyl)-2,4-pyrimidinedione and 2-chloro-6-picolyl bromide were reacted by the same way with the example 1 to obtain the titled compound (155 mg, yield: 37.6%).

Example 127

1-(2-Bromopyridin-6-ylmethyl)-5-ethyl-6-(3,5-dimethylphenoxy)-2,4-pyrimidinedione 5-Ethyl-6-(3,5-dimethylphenoxy)-2,4-pyrimidinedione and 2-bromo-6-picolyl bromide were reacted by the same way with the example 1 to obtain the titled compound (143 mg, yield: 33.2%).

Example 128

1-(2-Bromopyridin-6-ylmethyl)-5-isopropyl-6-(3,5-dimethylphenoxy)-2,4-pyrimidinedione 5-Isopropyl-6-(3,5-dimethylphenoxy)-2,4-pyrimidinedione and 2-bromo-6-picolyl bromide were reacted by the same way with the example 1 to obtain the titled compound (167 mg, yield: 37.6%).

Example 129

1-(2-Bromopyridib-6-ylmethyl)-5-ethyl-6-(3,5-dimethyl-benzoyl)-2,4-pyrimidinedione 5-Ethyl-6-(3,5-dimethylbenzoyl)-2,4-pyrimidinedione and 2-bromo-6-picolyl bromide were reacted by the same way with the example 1 to obtain the titled compound (149 mg, yield: 35.3%).

Example 130

1-(2-Bromopyridin-6-ylmethyl)-5-isopropyl-6-(3,5-dimethyl-benzoyl)-2,4-pyrimidinedione 5-Isopropyl-6-(3,5-dimethylbenzoyl)-2,4-pyrimidinedione and 2-bromo-6-picolyl bromide were reacted by the same way with the example 1 to obtain the titled compound (148 mg, yield: 32.4%).

Example 131

1-(Quinolin-2-ylmethyl)-5-ethyl-6-(3,5-dimethylphenyl)-thio-2,4-pyrimidinedione

5-Ethyl-6-(3,5-dimethylphenyl)thio-2,4-pyrimidinedione and 2-chloromethyl quinoline were reacted by the same way with the example 1 to obtain the titled compound (138 mg, yield: 33.1%).

Example 132

1-(Quinolin-2-ylmethyl)-5-isopropyl-6-(3,5-dimethylphenyl)thio-2,4-pyrimidinedione 5-Isopropyl-6-(3,5-dimethylphenyl)thio-2,4-pyrimidinedione and 2-chloromethyl quinoline were reacted by the same way with the example 1 to obtain the titled compound (125 mg, yield: 29.0%).

Example 133

1-(Quinolin-2-ylmethyl)-5-ethyl-6-(3,5-dimethylphenoxy)-2,4-pyrimidinedione

5-Ethyl-6-(3,5-dimethylphenoxy)-2,4-pyrimidinedione and 2-chloromethyl quinoline were reacted by the same way with the example 1 to obtain the titled compound (130 mg, yield: 32.4%).

Example 134

1-(Quinolin-2-ylmethyl)-5-isopropyl-6-(3,5-dimethyl-phenoxy)-2,4-pyrimidinedione 5-Isopropyl-6-(3,5-dimethylphenoxy)-2,4-pyrimidinedione and 2-chloromethyl quinoline were reacted by the same way with the example 1 to obtain the titled compound (139 mg, yield: 33.5%).

Example 135

1-(Quinolin-2-ylmethyl)-5-ethyl-6-(3,5-dimethylbenzoyl)-2,4-pyrimidinedione

5-Ethyl-6-(3,5-dimethylbenzoyl)-2,4-pyrimidinedione and 2-chloromethyl quinoline were reacted by the same way with the example 1 to obtain the titled compound (159 mg, yield: 38.5%).

Example 136

1-(Quinolin-2-ylmethyl)-5-isopropyl-6-(3,5-dimethyl-benzoyl)-2,4-pyrimidinedione 5-Isopropyl-6-(3,5-dimethylbenzoyl)-2,4-pyrimidinedione and 2-chloromethyl quinoline were reacted by the same way with the example 1 to obtain the titled compound (170 mg, yield: 39.8%).

Example 137

1-(2,3-Epoxypropyl)-5-ethyl-6-(3,5-dimethylphenoxy)-2,4 -pyrimidinedione 1) 1-Allyl-5-ethyl-6-(3,5-dimethylphenoxy)-2,4-pyrimidinedione To a solution of 5-ethyl-6-(3,5-dimethylphenoxy)-2,4-pyrimidinedione (258 mg, 1.0 mmol) and allyl bromide(121 mg, 1.0 mmol) dissolved in dimethylformamide(5 ml), sodium bicarbonate(126 mg, 1.50 mmol) and lithium iodide (13.0 mg, 0.10 mmol) were added and stirred at 90° C. for 24 hours. The resulting product was distilled under the reduced pressure to remove dimethylformamide and purified by column chromatography to obtain the titled compound as a white solid(157 mg, yield: 52.3%).

2) 1-(2,3-Epoxypropyl)-5-ethyl-6-(3,5-dimethylphenoxy)-2,4-pyrimidinedione

1-Allyl-5-ethyl-6-(3,5-dimethylphenoxy)-2,4-pyrimidinedione 157 mg, 0.52 mmol) was dissolved in dichloromethane (10 ml), and thereto chloro perbenzoic acid (385 mg, 1.56 mmol) was added. The resulting solution was refluxed for 24 hours, washed with a saturated solution of sodium bicarbonate, distilled under the reduced pressure to remove the used solvent and purified with column chromatography to obtain the titled compound as white solid (57 mg, yield: 35.0%).

Example 138

1-(2,3-Epoxypropyl)-5-isopropyl-6-(3,5-dimethylphenoxy)-2,4-pyrimidinedione 1) 1-Allyl-5-isopropyl-6-(3,5-dimethylphenoxy)-2,4-pyrimidinedione 5-Isopropyl-6-(3,5-dimethylphenoxy)-2,4-pyrimidinedione and allyl bromide were reacted by the same way with the example 45-1 to obtain the titled compound (225 mg, yield: 75.1%).

2) 1-(2,3-Epoxypropyl)-5-isopropyl-6-(3,5-dimethylphenoxy)-2,4-pyrimidinedione

1-Allyl-5-isopropyl-6-(3,5-dimethylphenoxy)-2,4-pyrimidinedione was reacted by the same way with the example 45-2 to obtain the titled compound (80 mg, yield: 37.2%).

Example 139

1-(2,3-Epoxypropyl)-5-ethyl-6-(3,5-dimethylbenzoyl)-2,4-pyrimidinedione 1) 1-Allyl-5-ethyl-6-(3,5-dimethylbenzoyl)-2,4-pyrimidinedione 5-Ethyl-6-(3,5-dimethylbenzoyl)-2,4-pyrimidinedione and allyl bromide were reacted by the same way with the example 45-1 to obtain the titled compound (190 mg, yield: 60.8%).

2) 1-(2,3-Epoxypropyl)-5-ethyl-6-(3,5-dimethylbenzoyl)-2,45 pyrimidinedione

1-Allyl-5-ethyl-6-(3,5-dimethylbenzoyl)-2,4-pyrimidinedione was reacted by the same way with the example 45-2 to obtain the titled compound (73 mg, yield: 40.3%).

Example 140

1-(2,3-Epoxypropyl)-5-isopropyl-6-(3,5-dimethylbenzoyl)-2,4-pyrimidinedione 1) 1-Allyl-5-isopropyl-6-(3,5-dimethylbenzoyl)-2,4-pyrimidinedione 5-Isopropyl-6-(3,5-dimethylbenzoyl)-2,4-pyrimidinedione and allyl bromide were reacted by the same way with the example 45-1 to obtain the titled compound (211 mg, yield: 64.3%).

2) 1-(2,3-Epoxypropyl)-5-isopropyl-6-(3,5-dimethylbenzoyl)-2,4-pyrimidinedione

1-Allyl-5-isopropyl-6-(3,5-dimethylbenzoyl)-2,4-pyrimidinedione was reacted by the same way with the example 45-2 to obtain the titled compound (86 mg, yield: 39.0%).

Example 141

1-(1H-benzotriazol-1-ylmethyl)-5-ethyl-6-(3,5-dimethylphenoxy)-2,4-pyrimidinedione 5-Ethyl-6-(3,5-dimethylphenoxy)-2,4-pyrimidinedione and 1-chloromethyl-1H-benzotriazole were reacted by the same way with the example 1 to obtain the titled compound (112 mg, yield: 28.6%).

Example 142

1-(1H-benzotriazol-1-ylmethyl)-5-isopropyl-6-(3,5-dimethylphenoxy)-2,4-pyrimidinedione 5-Isopropyl-6-(3,5-dimethylphenoxy)-2,4-pyrimidinedione and 1-chloromethyl-1H-benzotriazole were reacted by the same way with the example 1 to obtain the titled compound (108 mg, yield: 26.6%).

Example 143

1-(1H-benzotriazol-1-ylmethyl)-5-ethyl-6-(3,5-dimethylbenzoyl)-2,4-pyrimidinedione 5-Ethyl-6-(3,5-dimethylbenzoyl)-2,4-pyrimidinedione and 1-chloromethyl-1H-benzotriazole were reacted by the same way with the example 1 to obtain the titled compound (135 mg, yield: 33.5%).

Example 144

1-(1H-benzotriazol-1-ylmethyl)-5-isopropyl-6-(3,5-dimethyl-benzoyl)-2,4-pyrimidinedione 5-Isopropyl-6-(3,5-dimethylbenzoyl)-2,4-pyrimidinedione and 1-chloromethyl-1H-benzotriazole were reacted by the same way with the example 1 to obtain the titled compound (152 mg, yield: 36.4%).

Example 145

1-(Benzoxazol-2-ylmethyl)-5-ethyl-6-(3,5-dimethylphenyl)thio-2,4-pyrimidinedione 5-Ethyl-6-(3,5-dimethylphenyl)thio-2,4-pyrimidinedione and 2-chloromethyl benzoxazole were reacted by the same way with the example 1 to obtain the titled compound (176 mg, yield: 43.2%).

Example 146

1-(Benzoxazol-2-ylmethyl)-5-isopropyl-6-(3,5-dimethylphenyl)thio-2,4-pyrimidinedione 5-Isopropyl-6-(3,5-dimethylphenyl)thio-2,4-pyrimidinedione and 2-chloromethyl benzoxazole were reacted by the same way with the example 1 to obtain the titled compound (189 mg, yield: 44.8%).

Example 147

1-(Benzoxazol-2-ylmethyl)-5-ethyl-6-(3,5-dimethylphenoxy)-2,4-pyrimidinedione

5-Ethyl-6-(3,5-dimethylphenoxy)-2,4-pyrimidinedione and 2-chloromethyl benzoxazole were reacted by the same way with the example 1 to obtain the titled compound (215 mg, yield: 54.9%).

Example 148

1-(Benzoxazol-2-ylmethyl)-5-isopropyl-6-(3,5-dimethylphenoxy)-2,4-pyrimidinedione 5-Isopropyl-6-(3,5-dimethylphenoxy)-2,4-pyrimidinedione and 2-chloromethyl benzoxazole were reacted by the same way with the example 1 to obtain the titled compound (207 mg, yield: 51.1%).

Example 149

1-(Benzoxazol-2-ylmethyl)-5-ethyl-6-(3,5-dimethylbenzoyl)-2,4-pyrimidinedione

5-Ethyl-6-(3,5-dimethylbenzoyl)-2,4-pyrimidinedione and 2-chloromethyl benzoxazole were reacted by the same way with the example 1 to obtain the titled compound (241 mg, yield: 59.7%).

Example 150

1-(Benzoxazol-2-ylmethyl)-5-isopropyl-6-(3,5-dimethyl-benzoyl-2,4-pyrimidinedione 5-Isopropyl-6-(3,5-dimethylbenzoyl)-2,4-pyrimidinedione and 2-chloromethyl benzoxazole were reacted by the same way with the example 1 to obtain the titled compound (236 mg, yield: 56.5%).

Example 151

1-(3-Methoxycarbonyl-2-furanylmethyl)-5-ethyl-6-(3,55 dimethylphenyl)thio-2,4-pyrimidinedione 5-Ethyl-6-(3,5-dimethylphenyl)thio-2,4-pyrimidinedione and 2-bromomethyl-3-methoxycarbonylfurane were reacted by the same way with the example 1 to obtain the titled compound (125 mg, yield: 31.4%).

Example 152

1-(3-Methoxycarbonyl-2-furanylmethyl)-5-isopropyl-6-(3,5-dimethylphenyl)thio-2,4-pyrimidinedione 5-Isopropyl-6-(3,5-dimethylphenyl)thio-2,4-pyrimidinedione and 2-bromomethyl-3-methoxycarbonylfurane were reacted by the same way with the example 1 to obtain the titled compound (139 mg, yield: 33.7%).

Example 153

1-(3-Methoxycarbonyl-2-furanylmethyl)-5-ethyl-6-(3,5-dimethylphenoxy)-2,4-pyrimidinedione 5-Ethyl-6-(3,5-dimethylphenoxy)-2,4-pyrimidinedione and 2-bromomethyl-3-methoxycarbonylfurane were reacted

Example 154

1-(3-Methoxycarbonyl-2-furanylmethyl)-5-isopropyl-6-(3,5-dimethylphenoxy)-2,4-pyrimidinedione 5-Isopropyl-6-(3,5-dimethylphenoxy)-2,4-pyrimidinedione and 2-bromomethyl-3-methoxycarbonylfurane were reacted by the same way with the example 1 to obtain the titled compound (133 mg, yield: 33.5%).

Example 155

1-(3-Methoxycarbonyl-2-furanylmethyl)-5-ethyl-6-(3,5-dimethyl-benzoyl)-2,4-pyrimidinedione 5-Ethyl-6-(3,5-dimethylbenzoyl)-2,4-pyrimidinedione and 2-bromomethyl-3-methoxycarbonylfurane were reacted by the same way with the example 1 to obtain the titled compound (150 mg, yield: 38.0%).

Example 156

1-(3-Methoxycarbonyl-2-furanylmethyl)-5-isopropyl-6-(3,5-dimethyl-benzoyl)-2,4-pyrimidinedione 5-Isopropyl-6-(3,5-dimethylbenzoyl)-2,4-pyrimidinedione and 2-bromomethyl-3-methoxycarbonylfurane were reacted by the same way with the example 1 to obtain the titled compound (162 mg, yield: 39.7%).

Example 157

1-(Acetonyl)-5-ethyl-6-(3,5-dimethylphenoxy)-2,4-pyrimidinedione

5-Ethyl-6-(3,5-dimethylphenoxy)-2,4-pyrimidinedione and chloroacetone were reacted by the same way with the example 1 to obtain the titled compound (172 mg, yield: 54%).

Example 158

1-(Acetonyl)-5-isopropyl-6-(3,5-dimethylphenoxy)-2,4-pyrimidinedione

5-Isopropyl-6-(3,5-dimethylphenoxy)-2,4-pyrimidinedione and chloroacetone were reacted by the same way with the example 1 to obtain the titled compound (155 mg, yield: 45%).

Example 159

1-(Acetonyl)-5-ethyl-6-(3,5-dimethylbenzoyl)-2,4-pyrimidinedione

5-Ethyl-6-(3,5-dimethylbenzoyl)-2,4-pyrimidinedione and chloroacetone were reacted by the same way with the example 1 to obtain the titled compound (145 mg, yield: 44%).

Example 160

1-(Acetonyl)-5-isopropyl-6-(3,5-dimethylbenzoyl)-2,4-pyrimidinedione

5-Isopropyl-6-(3,5-dimethylbenzoyl)-2,4-pyrimidinedione and chloroacetone were reacted by the same way with the example 1 to obtain the titled compound (155 mg, yield: 45%).

Example 161

1-(2-Butanon-1-yl)-5-ethyl-6-(3,5-dimethylphenoxy)-2,4-pyrimidinedione

5-Ethyl-6-(3,5-dimethylphenoxy)-2,4-pyrimidinedione and 1-bromo-2-butanone were reacted by the same way with the example 1 to obtain the titled compound (185 mg, yield: 56%).

Example 162

1-(2-Butanon-1-yl)-5-isopropyl-6-(3,5-dimethylphenoxy)-2,4-pyrimidinedione

5-Isopropyl-6-(3,5-dimethylphenoxy)-2,4-pyrimidinedione and 1-bromo-2-butanone were reacted by the same way with the example 1 to obtain the titled compound (179 mg, yield: 49%).

Example 163

1-(2-Butanon-1-yl)-5-ethyl-6-(3,5-dimethylbenzoyl) δ 2,4-pyrimidinedione

5-Ethyl-6-(3,5-dimethylbenzoyl)-2,4-pyrimidinedione and 1-bromo-2-butanone were reacted by the same way with the example 1 to obtain the titled compound (182 mg, yield: 53%).

Example 164

1-(2-Butanon-1-yl)-5-isopropyl-6-(3,5-dimethylbenzoyl)-2,4-pyrimidinedione

5-Isopropyl-6-(3,5-dimethylbenzoyl)-2,4-pyrimidinedione and 1-bromo-2-butanone were reacted by the same way with the example 1 to obtain the titled compound (196 mg, yield: 55%).

Example 165

1-(Phenacyl)-5-ethyl-6-(3,5-dimethylphenoxy)-2,415 pyrimidinedione

5-Ethyl-6-(3,5-dimethylphenoxy)-2,4-pyrimidinedione and 2-chloroacetophenone were reacted by the same way with the example 1 to obtain the titled compound (164 mg, yield: 43%).

Example 166

1-(Phenacyl)-5-isopropyl-6-(3,5-dimethylphenoxy)-2,420 pyrimidinedione

5-Isopropyl-6-(3,5-dimethylphenoxy)-2,4-pyrimidinedione and 2-chloroacetophenone were reacted by the same way with the example 1 to obtain the titled compound (181 mg, yield: 46%).

Example 167

1-(Phenacyl)-5-ethyl-6-(3,5-dimethylbenzoyl)-2,4-pyrimidinedione

5-Ethyl-6-(3,5-dimethylbenzoyl)-2,4-pyrimidinedione and 2-chloroacetophenone were reacted by the same way with the example 1 to obtain the titled compound (210 mg, yield: 54%).

Example 168

1-(Phenacyl)-5-isopropyl-6-(3,5-dimethylbenzoyl)-2,4-pyrimidinedione

5-Isopropyl-6-(3,5-dimethylbenzoyl)-2,4-pyrimidinedione and 2-chloroacetophenone were reacted by the same way with the example 1 to obtain the titled compound (164 mg, yield: 43%).

Physical properties of the compounds prepared by the above examples are as follows:

| Ex. No. | m.p. (° C.) | NMR($^1$H NMR(CDCl$_3$)) |
|---|---|---|
| 1 | 161~163 | δ 0.42(2H, m), 0.47(2H, m), 1.04(3H, t), 1.20(1H, m), 2.28(6H, s), 2.70(1H, q), 3.90(2H, d), 6.75(2H, s), 6.87(1H, s), 9.11(1H, s) |
| 2 | 139~141 | δ 0.42(2H, m), 0.46(2H, m), 1.22(3H, s), 1.23(3H, s), 1.36(1H, m), 2.28(6H, s), 3.51(1H, m), 3.95(2H, d), 6.77(2H, s), 6.86(1H, s), 9.39(1H, s) |
| 3 | 190~192 | δ 0.35(2H, m), 0.49(2H, m), 0.95(3H, t), 1.18(1H, m), 2.21(2H, q), 2.31(6H, s), 3.62(2H, d), 6.55(2H, s), 6.77(1H, s), 8.84(1H, s) |
| 4 | 146~148 | δ 0.33(2H, m), 0.46(2H, m), 1.14(3H, s), 1.15(3H, s), 1.34(1H, m), 2.18(6H, s), 2.76(1H, m), 3.57(2H, d), 6.54(2H, s), 6.77(1H, s), 9.07(1H, s) |
| 5 | 234~236 | δ 0.25(2H, m), 0.42(2H, m), 0.97(3H, t), 1.00(1H, m), 2.02(1H, m), 2.27(1H, m), 2.40(6H, s), 3.30(1H, m), 3.65(1H, m), 7.34(1H, s), 7.54(2H, s), 8.89(1H, s) |
| 6 | 193~195 | δ 0.23(2H, m), 0.39(2H, m), 0.99(1H, m), 1.13(3H, d), 1.24(3H, d), 2.33(1H, m), 2.41(6H, s), 3.30(1H, m), 3.59(1H, m), 7.34(1H, s), 7.56(2H, s), 9.05(1H, s) |
| 7 | 140~142 | δ 1.02(3H, t), 1.80(4H, m), 1.96(2H, m), 2.28(6H, s), 2.61(1H, m), 2.67(2H, q), 4.03(2H, d), 6.73(2H, s), 6.88(1H, s), 9.04(1H, s) |
| 8 | 136~138 | δ 1.20(3H, s), 1.21(3H, s), 1.82(4H, m), 1.97(2H, m), 2.28(6H, s), 2.69(1H, m), 3.50(1H, m), 4.10(2H, d), 6.73(2H, s), 6.87(1H, s), 9.12(1H, s) |
| 9 | 193~195 | δ 0.93(3H, t), 1.73(4H, m), 1.99(2H, m), 2.19(2H, q), 2.32(6H, s), 2.67(1H, m), 3.76(2H, d), 6.53(2H, s), 6.79(1H, s), 8.59(1H, s) |
| 10 | 106~108 | δ 1.13(3H, d), 1.29(3H, d), 1.69(4H, m), 1.99(2H, m), 2.32(6H, s), 2.65(1H, m), 2.78(1H, m), 3.71(2H, d), 6.52(2H, s), 6.68(1H, s), 9.07(1H, s) |
| 11 | 200~202 | δ 0.96(3H, t), 1.64(4H, m), 1.90(2H, m), 1.99(1H, m), 2.24(1H, m), 2.40(6H, s), 2.54(2H, m), 3.23(1H, m), 3.93(1H, m), 7.34(1H, s), 7.49(2H, s), 8.47(1H, s) |
| 12 | 171~173 | δ 1.11(3H, d), 1.21(3H, d), 1.65(4H, m), 1.89(2H, m), 2.31(1H, m), 2.41(6H, s), 2.52(2H, m), 3.22(1H, m), 3.84(1H, m), 7.35(1H, s), 7.52(2H, s), 8.26(1H, s) |
| 13 | 191~193 | δ 1.03(3H, t), 1.04(2H, m), 1.15(3H, m), 1.58(2H, m), 1.71(3H, m), 2.28(6H, s), 2.32(6H, m), 2.69(2H, q), 3.83(2H, d), 6.73(2H, s), 6.86(1H, s), 8.62(1H, s) |
| 14 | 180~182 | δ 1.03(2H, m), 1.14(3H, m), 1.20(3H, s), 1.22(3H, s), 1.57(2H, m), 1.75(3H, m), 2.28(6H, s), 3.51(1H, m), 3.91(2H, d), 6.74(2H, s), 6.87(1H, s), 9.17(1H, s) |
| 15 | 194~196 | δ 0.94(3H, t), 0.98(2H, m), 1.18(3H, m), 1.63(2H, m), 1.76(3H, m), 2.22(2H, q), 2.31(6H, s), 3.54(2H, d), 6.52(2H, s), 6.75(1H, s), 8.64(1H, s) |
| 16 | 171~173 | δ 1.14(3H, s), 1.15(3H, s), 1.18(2H, m), 1.27(3H, m), 1.60(2H, m), 1.72(3H, m), 2.31(6H, s), 2.80(1H, m), 3.47(2H, d), 6.51(2H, s), 6.77(1H, s), 8.89(1H, s) |
| 17 | 177~179 | δ 0.87(3H, m), 0.97(3H, t), 1.09(3H, m), 1.48(2H, m), 1.57(3H, m), 2.03(1H, m), 2.26(1H, m), 2.40(6H, s), 3.06(1H, m), 3.74(1H, m), 7.34(1H, s), 7.44(2H, s), 8.75(1H, s) |
| 18 | 160~162 | δ 0.85(2H, m), 1.07(2H, m), 1.11(3H, d), 1.22(3H, d), 1.43(4H, m), 1.75(2H, m), 2.33(1H, m), 2.41(6H, s), 3.07(1H, m), 3.68(1H, m), 7.35(1H, s), 7.52(2H, s), 8.47(1H, s) |
| 19 | 202~204 | δ 1.01(3H, t), 2.25(6H, s), 2.68(2H, q), 5.21(2H, s), 6.69(2H, s), 6.85(1H, s), 7.25(5H, m), 8.66(1H, s) |
| 20 | 196~198 | δ 1.19(3H, s), 1.21(3H, s), 2.25(6H, s), 3.49(1H, m), 5.27(2H, s), 6.67(2H, s), 6.84(1H, s), 7.24(5H, m), 8.51(1H, s) |
| 21 | 192~194 | δ 0.91(3H, t), 2.19(2H, q), 2.27(6H, s), 4.92(2H, s), 6.46(2H, s), 6.71(1H, s), 7.27(5H, s), 8.99(1H, s) |
| 22 | 200~202 | δ 1.10(3H, s), 1.12(3H, s), 2.28(6H, s), 2.77(1H, m), 4.87(2H, s), 6.47(2H, s), 6.75(1H, s), 7.26(5H, m), 8.76(1H, s) |
| 23 | 202~204 | δ 0.93(3H, t), 2.00(1H, m), 2.22(1H, m), 2.27(6H, s), 4.63(1H, d), 5.05(1H, d), 7.05(2H, m), 7.11(3H, m), 7.19(1H, s), 7.26(2H, s), 8.80(1H, s) |
| 24 | 188~190 | δ 1.08(3H, d), 1.21(3H, d), 2.27(6H, s), 2.31(1H, m), 4.58(1H, d), 5.05(1H, d), 7.04(2H, m), 7.10(3H, m), 7.18(1H, s), 7.26(2H, s), 8.93(1H, s) |
| 25 | 130~131 | δ 1.01.(3H, t), 2.25(6H, s), 2.69(2H, q), 3.75(3H, s), 5.18(2H, s), 6.69(2H, s), 6.72(1H, s), 6.76(2H, t) |
| 26 | 135~137 | δ 1.19(6H, m), 2.24(6H, s), 3.48(1H, m), 3.75(3H, s), 5.24(2H, s), 6.67(2H, s), 6.73(1H, s), 6.77(2H, s), 6.83(1H, s), 7.20(1H, t), 8.64(1H, s) |
| 27 | 133~135 | δ 0.91(3H, t), 2.17(2H, q), 2.27(6H, s), 3.74(3H, s), 4.89(2H, s), 6.45(2H, s), 6.74(1H, s), 6.78(2H, s), 6.85(1H, d), 7.19(1H, t), 8.67(1H, s) |
| 28 | 158~159 | δ 1.10(6H, d), 2.27(6H, s), 2.75(1H, m), 3.79(3H, s), 4.84(2H, s), 6.46(2H, s), 6.74(1H, s), 6.79(2H, d), 6.83(1H, d), 7.19(1H, t), 8.76(1H, s) |
| 29 | 185~187 | δ 0.92(3H, t), 2.01(1H, m), 2.19(1H, m), 2.27(6H, s), 3.64(3H, s), 4.53(1H, d, J=15.7Hz), 5.10(1H, d, J=15.7Hz), 6.54(1H, s), 6.62(2H, m), 7.03(1H, t), 7.18(1H, s), 7.26(2H, br), 8.72(1H, s) |
| 30 | 184~186 | δ 1.08(3H, d, J=6.8Hz), 1.20(3H, d, J=6.8Hz), 2.27(6H, s), 2.31(1H, m), 3.64(3H, s), 4.49(1H, d, J=15.7Hz), 5.12(1H, d, J=15.7Hz), 6.53(1H, s), 6.58(1H, m), 6.64(1H, d), 7.02(1H, t), 7.17(1H, s), 7.26(2H, br), 9.35(1H, s) |
| 31 | 138~140 | δ 1.03(3H, t), 2.23(6H, s), 2.70(2H, q), 5.21(2H, s), 6.67(2H, s), 6.82(2H, s), 7.07(2H, d), 7.20(2H, d), 8.84(1H, s) |
| 32 | 124~126 | δ 1.21(6H, d), 2.22(6H, s), 3.50(1H, m), 5.26(2H, s), 6.65(2H, s), 6.82(2H, s), 7.08(1H, s), 7.21(2H, d), 8.41(1H, s) |
| 33 | 148~150 | δ 0.91(3H, t), 2.17(2H, q), 2.26(6H, s), 4.91(2H, s), 6.44(2H, s), 6.75(1H, s), 7.09(2H, d), 7.29(2H, d), 8.60(1H, s) |
| 34 | 173~175 | δ 1.10(6H, d), 2.27(6H, s), 2.74(1H, m), 4.87(2H, s), 6.45(2H, s), 6.74(1H, s), 7.09(2H, d), 7.29(2H, d), 8.60(1H, s) |
| 35 | 155~157 | δ 0.94(3H, t), 2.01(1H, m), 2.21(1H, m), 2.28(6H, s), 4.60(1H, d, J=15.8Hz), 5.05(1H, d, J=15.8Hz), 6.94(2H, d), 7.09(2H, d), 7.21(1H, s), 7.26(2H, s), 8.88(1H, s) |
| 36 | 79~81 | δ 1.08(3H, d, J=6.8Hz), 1.20(3H, d, J=6.8Hz), 2.28(6H, s), 2.31(1H, m), 4.54(1H, d, J=15.8Hz), 5.06(1H, d, J=15.8Hz), 6.92(2H, d), 7.07(2H, d), 7.21(1H, s), 7.26(2H, br), 8.57(1H, s) |
| 37 | 221~223 | δ 1.09(3H, t), 2.20(6H, s), 2.76(2H, q), 5.45(2H, s), 6.72(2H, s), 6.74(1H, s), 6.93(1H, d), 7.24(1H, t), 7.43(1H, t), 7.53(1H, d), 8.66(1H, s) |
| 38 | 238~240 | δ 1.28(6H, d), 2.20(6H, s), 3.56(1H, m), 5.50(2H, s), 6.69(2H, s), 6.75(1H, s), 6.97(1H, d), 7.26(1H, t), 7.45(1H, t), 7.54(1H, d), 8.67(1H, s) |
| 39 | 267~270 | δ 0.93(3H, t), 2.18(2H, q), 2.20(6H, s), 5.22(2H, s), 6.36(2H, s), 6.66(1H, s), 7.30(2H, t), 7.47(1H, d), 7.54(1H, t), 8.74(1H, s) |
| 40 | 276~278 | δ 1.12(6H, d), 2.21(6H, s), 2.76(1H, m), 5.17(2H, s), 6.37(2H, s), 6.64(1H, s), 7.28(2H, t), 7.45(1H, d), 7.53(1H, t), 8.52(1H, s) |

| Ex. No. | m.p. (° C.) | NMR(¹H NMR(CDCl₃)) |
|---|---|---|
| 41 | 257~259 | δ 0.98(3H, t), 2.07(1H, m), 2.27(1H, m), 2.33(6H, s), 4.84(1H, d, J=16.5Hz), 5.14(1H, d, J=16.5Hz), 7.28(1H, s), 7.32(2H, m), 7.39(2H, br), 7.45(1H, d), 7.54(1H, t), 8.83(1H, s) |
| 42 | 250~253 | δ 1.14(3H, d, J=6.75Hz), 1.23(3H, d, J=6.75Hz), 2.33(6H, s), 2.37(1H, m), 4.82(1H, d, J=16.9Hz), 5.11(1H, d, J=16.9Hz), 7.28(1H, d), 7.32(1H, d), 7.41(2H, br), 7.44(2H, d), 7.55(1H, t), 8.76(1H, s) |
| 43 | 179~181 | δ 1.06(3H, t), 2.23(6H, s), 2.74(2H, q), 5.23(2H, s), 6.65(2H, s), 6.82(1H, s), 7.34(2H, m), 7.41(1H, d), 7.46(1H, d), 8.78(1H, s) |
| 44 | 186~188 | δ 1.25(6H, d), 2.23(6H, s), 3.51(1H, m), 5.29(2H, s), 6.63(2H, s), 6.82(1H, s), 7.35(2H, m), 7.43(1H, d), 7.46(1H, d), 8.92(1H, s) |
| 45 | 213~214 | δ 0.92(3H, t), 2.19(2H, q), 2.27(6H, s), 4.95(2H, s), 6.43(2H, s), 6.76(1H, s), 7.39(1H, t), 7.49(1H, s), 7.54(2H, m), 9.24(1H, s) |
| 46 | 160~162 | δ 1.11(6H, d), 2.27(6H, s), 2.75(1H, m), 4.91(2H, s), 6.43(2H, s), 6.75(1H, s), 7.38(1H, t), 7.46(1H, s), 7.53(2H, t), 9.30(1H, s) |
| 47 | 206~207 | δ 0.96(3H, t), 2.02(1H, m), 2.24(1H, m), 2.31(6H, s), 4.63(1H, d, J=15.8Hz), 5.02(1H, d, J=15.8Hz), 7.27(3H, m), 7.30(2H, t), 7.41(2H, d), 9.11(1H, s) |
| 48 | 202~204 | δ 1.11(3H, d, J=6.8Hz), 1.22(3H, d, J=6.8Hz), 2.31(6H, s), 2.32(1H, m), 4.58(1H, d, J=15.9Hz), 5.04(1H, d, J=15.9Hz), 7.23(1H, s), 7.25(2H, s), 7.28(2H, t), 7.39(2H, d), 9.03(1H, s) |
| 49 | 180~182 | δ 1.02(3H, t), 2.24(6H, s), 2.70(2H, q), 5.16(2H, s), 6.67(2H, s), 6.76(1H, s), 6.83(2H, s), 9.16(1H, s) |
| 50 | 164~166 | δ 1.14(3H, s), 1.15(3H, s), 2.21(12H, s), 2.80(1H, m), 5.22(2H, s), 6.59(2H, s), 6.72(21.02(3H, t), 6.80(2H, s), 9.21(1H, s) |
| 51 | 130~132 | δ 1.02(3H, t), 2.12(2H, q), 2.28(6H, s), 5.09(2H, s), 6.49(2H, s), 6.60(2H, s), 6.75(2H, s), 9.05(1H, s) |
| 52 | 175~177 | δ 1.13(3H, s), 1.15(3H, s), 2.25(12H, s), 2.65(1H, m), 5.25(2H, s), 6.50(2H, s), 6.62(2H, s), 6.79(2H, s), 9.01(1H, s) |
| 53 | 188~190 | δ 0.92(3H, t), 2.00(1H, m), 2.09(6H, s), 2.21(1H, m), 2.25(6H, s), 4.37(1H, d), 5.23(1H, d), 6.58(2H, s), 6.67(1H, s), 7.15(2H, s), 7.26(1H, s), 8.71(1H, s) |
| 54 | 228~230 | δ 1.08(3H, d), 1.20(3H, d), 2.08(6H, s), 2.25(6H, s), 2.29(1H, m), 4.32(1H, d), 5.25(1H, d), 6.58(2H, s), 6.65(1H, s), 7.14(2H, s), 7.21(1H, s), 9.13(1H, s) |
| 55 | 181~183 | δ 1.02(3H, t), 2.24(6H, s), 2.70(2H, q), 3.73(6H, s), 5.15(2H, s), 6.30(3H, s), 6.69(2H, s), 6.83(2H, s), 8.92(1H, s) |
| 56 | 157~160 | δ 1.20(6H, d), 2.21(6H, s), 3.48(1H, m), 3.73(6H, s), 5.21(2H, s), 6.31(1H, s), 6.32(2H, s), 6.68(2H, s), 6.83(1H, s), 8.81(1H, s) |
| 57 | 154~156 | δ 0.91(3H, t), 2.17(2H, q), 2.27(6H, s), 3.72(6H, s), 4.85(2H, s), 6.33(1H, s), 6.39(2H, s), 6.45(2H, s), 6.74(1H, s), 8.48(1H, s) |
| 58 | 162~164 | δ 1.10(6H, d), 2.27(6H, s), 2.75(1H, m), 3.72(6H, s), 4.80(2H, s), 6.33(1H, s), 6.38(2H, s), 6.46(2H, s), 6.74(1H, s), 8.65(1H, s) |
| 59 | 208~210 | δ 0.93(3H, t), 2.00(1H, m), 2.22(1H, m), 2.27(6H, s), 3.63(6H, s), 4.43(1H, d, J=15.6Hz), 5.15(1H, d, J=15.6Hz), 6.14(1H, s), 6.16(2H, s), 7.18(1H, s), 7.26(2H, s), 8.57(1H, s) |
| 60 | 220~222 | δ 1.08(3H, d, J=6.8Hz), 1.19(3H, d, J=6.8Hz), 2.27(6H, s), 2.29(1H, m), 3.63(6H, s), 4.37(1H, d, J=15.7Hz), 5.16(1H, d, J=15.7Hz), 6.11(1H, s), 6.14(2H, s), 7.17(1H, s), 7.26(2H, s), 8.61(1H, s) |
| 61 | 212~213 | δ 1.08(3H, t), 2.17(6H, s), 2.75(2H, q), 5.34(2H, s), 6.60(2H, s), 6.75(1H, s), 7.50(2H, s), 7.65(1H, s), 8.86(1H, s) |
| 62 | 183~185 | δ 1.27(6H, d), 2.17(6H, s), 3.51(1H, m), 5.39(2H, s), 6.57(2H, s), 6.75(1H, s), 7.54(2H, s), 7.63(1H, s), 8.89(1H, s) |
| 63 | 183~185 | δ 0.93(3H, t), 2.20(2H, q), 2.22(6H, s), 5.06(2H, s), 6.37(2H, s), 6.71(1H, s), 7.65(2H, s), 7.72(1H, s), 9.22(1H, s) |
| 64 | 182~183 | δ 1.13(6H, d), 2.22(6H, s), 2.73(1H, m), 5.01(2H, s), 6.36(2H, s), 6.69(1H, s), 7.62(2H, s), 7.71(1H, s), 8.68(1H, s) |
| 65 | 241~243 | δ 0.96(3H, t), 2.02(1H, m), 2.24(7H, s), 4.62(1H, d, J=15.9Hz), 5.28(1H, d, J=15.9Hz), 7.19(1H, s), 7.22(2H, br), 7.49(2H, s), 7.59(1H, s), 9.04(1H, s) |
| 66 | 178~180 | δ 1.11(3H, d, J=6.8Hz), 1.23(3H, d, J=6.8Hz), 2.24(6H, s), 2.30(1H, m), 4.59(1H, d, J=16.0Hz), 5.30(1H, d, J=16.0Hz), 7.18(1H, s), 7.20(2H, br), 7.48(2H, s), 7.57(1H, s), 9.19(1H, s) |
| 67 | 214~216 | δ 1.09(3H, t), 2.22(6H, s), 2.76(2H, q), 5.26(2H, s), 6.54(1H, m), 6.71(2H, s), 6.77(1H, s), 6.82(1H, m), 6.89(1H, m), 8.93(1H, s) |
| 68 | 192~194 | δ 1.28(6H, d), 2.22(6H, s), 3.55(1H, m), 5.31(2H, s), 6.58(1H, m), 6.70(2H, s), 6.78(1H, s), 6.82(1H, s), 6.91(1H, m), 8.86(1H, s) |
| 69 | 231~233 | δ 0.93(3H, t), 2.19(2H, q), 2.25(6H, s), 5.00(2H, s), 6.43(2H, s), 6.71(1H, s), 6.88(2H, m), 6.93(1H, m), 8.62(1H, s) |
| 70 | 214~216 | δ 1.22(6H, d), 2.25(6H, s), 2.76(1H, m), 4.96(2H, s), 6.43(2H, s), 6.70(1H, s), 6.87(2H, m), 6.90(1H, m), 8.57(1H, s) |
| 71 | 135~137 | δ 0.96(3H, t), 2.04(1H, m), 2.23(1H, m), 2.31(6H, s), 4.81(1H, d, J=16.3Hz), 4.92(1H, d, J=16.3Hz), 6.74(2H, m), 6.88(1H, m), 7.22(1H, s), 7.33(2H, br), 8.57(1H, s) |
| 72 | 205~207 | δ 1.13(3H, d, J=6.8Hz), 1.14(3H, d, J=6.8Hz), 2.31(6H, s), 2.34(1H, m), 4.79(1H, d, J=16.6Hz), 4.92(1H, d, J=16.6Hz), 6.70(2H, m), 7.22(1H, s), 7.35(2H, br), 9.06(1H, s) |
| 73 | 219~221 | δ 1.06(3H, t), 2.24(6H, s), 2.72(2H, q), 5.17(2H, s), 6.63(3H, m), 6.68(2H, s), 6.83(1H, s), 8.54(1H, s) |
| 74 | 203~205 | δ 1.25(6H, d), 2.24(6H, s), 3.52(1H, m), 5.23(2H, s), 6.63(5H, m), 6.82(1H, s), 9.04(1H, s) |
| 75 | 178~180 | δ 1.07(3H, t), 2.30(6H, s), 2.41(2H, q), 4.95(2H, s), 6.67(3H, m), 6.86(1H, m), 6.93(2H, d), 8.49(1H, s) |
| 76 | 186~189 | δ 1.12(6H, d), 2.28(6H, s), 2.76(1H, m), 4.84(2H, s), 6.46(2H, s), 6.68(1H, m), 6.75(3H, m), 9.00(1H, s) |
| 77 | 165~167 | δ 0.96(3H, t), 2.03(1H, m), 2.25(1H, m), 2.32(6H, s), 4.58(1H, d), 4.97(1H, d), 6.56(3H, m), 7.25(1H, s), 7.26(2H, s), 9.09(1H, s) |
| 78 | 207~209 | δ 1.12(3H, d, J=6.85Hz), 1.22(3H, d, J=6.85Hz), 2.35(7H, m), 4.52(1H, d, J=16.0Hz), 4.97(1H, d, J=16.0Hz), 6.56(3H, m), 7.24(1H, s), 7.34(2H, s), 8.89(1H, s) |
| 79 | 180~182 | δ 1.07(3H, t), 2.23(6H, s), 2.73(1H, q), 5.18(2H, s), 6.64(2H, s), 6.80(1H, s), 6.93(2H, s), 7.14(1H, s), 9.12(1H, s) |
| 80 | 194~196 | δ 1.26(6H, d), 2.23(6H, s), 3.52(1H, m), 5.23(2H, s), 6.62(2H, s), 6.80(1H, s), 6.96(2H, s), 7.14(1H, s), 8.79(1H, s) |
| 81 | 194~196 | δ 0.93(3H, t), 2.20(2H, q), 2.27(6H, s), 4.87(2H, s), 6.42(2H, s), 6.74(1H, s), 7.09(2H, d), 7.20(1H, s), 8.75(1H, s) |
| 82 | 234~236 | δ 1.12(6H, d), 2.27(6H, s), 2.75(1H, m), 4.83(2H, s), 6.42(2H, s), 6.73(1H, s), 7.06(2H, d), 7.20(1H, s), 8.75(1H, s) |
| 83 | 223~225 | δ 0.96(3H, t), 2.02(1H, m), 2.24(1H, m), 2.31(6H, s), 4.38(1H, d, J=15.9Hz), 5.17(1H, d, J=15.9Hz), 6.89(2H, s), 7.05(1H, s), 7.22(1H, s), 7.26(2H, br), 9.02(1H, s) |
| 84 | 220~222 | δ 1.12(3H, d, J=6.8Hz), 1.21(3H, d, J=6.8Hz), 2.31(6H, s), 2.33(3H, m), 4.33(1H, d, J=15.9Hz), 5.20(2H, d, J=15.9Hz), 6.88(2H, s), 7.03(1H, s), 7.21(1H, s), 7.26(2H, br), 9.03(1H, s) |
| 85 | 214~215 | δ 1.07(3H, t), 2.24(6H, s), 2.73(2H, q), 5.18(2H, s), 6.64(2H, s), 6.81(1H, s), 7.12(2H, s), 7.44(1H, s), 8.74(1H, s) |
| 86 | 225~226 | δ 1.26(6H, d), 2.24(6H, s), 3.52(1H, m), 5.23(2H, s), 6.61(2H, s), 6.80(1H, s), 7.15(2H, s), 7.44(1H, s), 8.77(1H, s) |
| 87 | 210~211 | δ 0.93(3H, t), 2.19(2H, q), 2.27(6H, s), 4.86(2H, s), 6.41(2H, s), 6.74(1H, s), 7.27(2H, s), 7.50(1H, s), 8.79(1H, s) |
| 88 | 244~246 | δ 1.12(6H, d), 2.27(6H, s), 2.74(1H, m), 4.83(2H, s), 6.40(2H, s), 6.72(1H, s), 7.24(2H, s), 7.49(1H, s), 8.86(1H, s) |

-continued

| Ex. No. | m.p. (° C.) | NMR(¹H NMR(CDCl₃)) |
|---|---|---|
| 89 | 234~236 | δ 0.95(3H, s), 2.02(1H, m), 2.24(1H, m), 2.31(6H, s), 4.33(1H, d, J=15.8Hz), 5.24(1H, d, J=15.8Hz), 7.07(2H, s), 7.22(1H, s), 7.28(2H, br), 7.35(1H, s), 8.95(1H, s) |
| 90 | 223~225 | δ 1.11(3H, d, J=6.8Hz), 1.21(3H, d, J=6.8Hz), 2.29(1H, m), 2.32(6H, s), 4.28(1H, d, J=15.8Hz), 5.25(1H, d, J=15.8Hz), 7.06(2H, s), 7.21(1H, s), 7.25(2H, br), 7.33(1H, s), 8.84(1H, s) |
| 91 | 173~176 | δ 1.02(3H, t), 2.15(6H, s), 2.69(2H, q), 5.40(2H, s), 6.64(2H, s), 6.70(1H, s), 7.32(1H, d), 7.44(2H, m), 7.55(1H, s), 7.73(3H, m), 9.10(1H, s) |
| 92 | 168~171 | δ 1.20(6H, d), 2.14(6H, s), 3.48(1H, m), 5.46(2H, s), 6.62(2H, s), 6.70(1H, s), 7.34(1H, s), 7.44(2H, m), 7.57(1H, s), 7.76(3H, m), 8.84(1H, s) |
| 93 | 181~183 | δ 0.90(3H, t), 2.17(2H, q), 2.18(6H, s), 5.10(2H, s), 6.42(2H, s), 6.66(1H, s), 7.40(1H, d), 7.45(2H, m), 7.64(1H, s), 7.71(1H, s), 7.78(2H, m), 8.65(1H, s) |
| 94 | 195~196 | δ 1.10(6H, d), 2.21(6H, s), 2.75(1H, m), 5.06(2H, s), 6.44(2H, s), 6.65(1H, s), 7.39(1H, m), 7.45(2H, m), 7.63(1H, s), 7.76(3H, m), 8.97(1H, s) |
| 95 | 242~244 | δ 0.91(3H, t), 2.01(6H, s), 2.19(2H, q), 4.61(1H, d, J=15.5Hz), 5.54(1H, d, J=15.5Hz), 6.78(1H, s), 7.06(2H, br), 7.21(1H, d), 7.29(1H, s), 7.35(1H, t), 7.41(1H, t), 7.49(1H, s), 7.60(1H, d), 7.65(1H, d), 9.06(1H, s) |
| 96 | 215~218 | δ 1.05(3H, d, J=6.8Hz), 1.20(3H, d, J=6.8Hz), 2.01(6H, s), 2.27(1H, m), 4.56(1H, d, J=15.5Hz), 5.56(1H, d, J=15.6Hz), 6.75(1H, s), 7.08(2H, br), 7.20(1H, d), 7.27(1H, s), 7.34(1H, t), 7.40(1H, t), 7.48(1H, s), 7.59(1H, d), 7.64(1H, d), 9.16(1H, s) |
| 97 | 219~220 | δ 0.98(3H, t), 1.99(6H, s), 2.00(2H, q), 5.85(2H, s), 6.20(2H, s), 6.60(1H, s), 7.39(2H, t), 7.47(2H, t), 7.84(2H, d), 8.14(1H, s), 8.18(2H, d), 8.78(1H, s) |
| 98 | 129~131 | δ 1.12(6H, d), 1.95(6H, s), 3.18(1H, m), 5.72(2H, s), 6.27(2H, s), 6.55(1H, s), 7.39(2H, t), 7.49(2H, t), 7.83(2H, d), 8.11(1H, s), 8.20(2H, d), 8.55(1H, s) |
| 99 | 243~245 | δ 0.72(3H, t), 1.72(6H, s), 1.83(2H, q), 5.02(2H, s), 6.20(2H, s), 7.38(2H, t), 7.53(2H, t), 7.76(2H, d), 8.01(1H, s), 8.29(2H, d), 8.80(1H, s) |
| 100 | 224~226 | δ 0.88(6H, d), 1.72(6H, s), 2.29(1H, m), 5.04(2H, s), 6.19(3H, s), 7.39(2H, t), 7.54(2H, t), 7.76(2H, d), 8.00(1H, s), 8.29(2H, d), 8.68(1H, s) |
| 101 | 270~272 | δ 0.73(3H, t), 1.66(2H, q), 1.99(6H, m), 5.35(1H, br), 5.57(1H, d, J=15.6Hz), 6.27(1H, br), 6.65(1H, d, J=15.6Hz), 6.75(1H, s), 7.40(2H, t), 7.60(2H, t), 7.68(2H, d), 7.81(1H, s), 8.07(2H, d), 9.18(1H, s) |
| 102 | 273~275 | δ 0.83(3H, t, J=6.75Hz), 1.03(3H, d, J=6.75Hz), 1.89(7H, m), 5.40(1H, br), 5.54(1H, d, J=15.6Hz), 6.20(1H, br), 6.64(1H, d, J=15.6Hz), 6.74(1H, s), 7.40(2H, t), 7.61(2H, t), 7.68(2H, d), 7.81(1H, s), 8.07(2H, d), 8.62(1H, s) |
| 103 | 195~197 | δ 1.12(3H, t), 2.10(6H, s), 2.56(2H, q), 5.40(2H, s), 6.57(1H, s), 6.63(2H, s), 7.47(2H, s), 7.78(2H, m), 7.80(1H, d), 8.18(1H, m), 8.24(2H, m), 8.29(1H, m), 8.85(1H, s) |
| 104 | 120~122 | δ 1.30(6H, d), 2.10(6H, s), 3.60(1H, m), 5.39(2H, s), 6.56(1H, s), 6.60(2H, s), 7.50(1H, d), 7.78(2H, m), 7.84(2H, d), 8.25(1H, d), 8.32(2H, d), 8.92(1H, s) |
| 105 | 233~235 | δ 0.94(3H, t), 2.19(8H, m), 5.10(2H, s), 6.41(2H, s), 6.59(1H, s), 7.66(1H, s), 7.82(1H, d), 8.07(1H, s), 8.22(1H, d), 8.31(2H, m), 8.49(2H, s) |
| 106 | 246~248 | δ 1.12(6H, d), 2.19(6H, s), 2.75(1H, m), 5.07(2H, s), 6.41(2H, s), 6.57(1H, s), 7.65(1H, s), 7.82(2H, m), 8.04(1H, s), 8.22(1H, s), 8.30(2H, s), 8.57(1H, s) |
| 107 | 143~146 | δ 0.96(3H, t), 2.02(1H, m), 2.14(6H, s), 2.24(1H, m), 4.75(1H, d, J=16.1Hz), 5.29(1H, d, J=16.1Hz), 6.91(1H, s), 7.24(2H, br), 7.56(2H, s), 7.82(3H, m), 8.13(1H, d), 8.27(2H, m) |
| 108 | 156~158 | δ 1.11(3H, d, J=6.75Hz), 1.21(3H, d, J=6.75Hz), 2.14(6H, s), 2.30(1H, m), 4.69(1H, d, J=16.1Hz), 5.31(1H, d, J=16.1Hz), 6.89(1H, s), 7.24(2H, br), 7.56(2H, s), 7.82(3H, m), 8.12(1H, d), 8.27(1H, d), 8.74(2H, m) |
| 109 | 217~219 | δ 1.05(3H, t), 2.22(6H, s), 2.72(2H, q), 5.38(2H, s), 6.71(2H, s), 6.78(1H, s), 6.97(1H, d), 7.11(1H, s), 7.56(1H, t), 8.46(1H, d), 8.63(1H, s) |
| 110 | 194~196 | δ 1.24(6H, d), 2.22(6H, s), 3.51(1H, m), 5.43(2H, s), 6.70(2H, s), 6.78(1H, s), 6.99(1H, d), 7.10(1H, t), 7.55(1H, t), 8.47(1H, d), 9.00(1H, s) |
| 111 | 215~217 | δ 0.93(3H, t), 2.20(2H, q), 2.23(6H, s), 5.10(2H, s), 6.45(2H, s), 6.68(1H, s), 7.13(2H, s), 7.60(1H, t), 8.48(1H, d), 8.81(1H, s) |
| 112 | 220~223 | δ 1.13(6H, d), 2.23(6H, s), 2.77(1H, m), 5.05(2H, s), 6.43(2H, s), 6.67(1H, s), 7.11(2H, m), 7.58(1H, m), 8.47(1H, d), 9.11(1H, s) |
| 113 | 153~155 | δ 0.95(3H, t), 2.04(1H, m), 2.23(1H, m), 2.29(6H, s), 4.83(1H, d, J=15.9Hz), 5.10(1H, d, J=15.9Hz), 7.05(2H, m), 7.19(1H, s), 7.39(2H, s), 7.51(1H, s), 8.40(1H, d), 8.76(1H, s) |
| 114 | 206~208 | δ 1.11(3H, d, J=6.8Hz), 1.21(3H, d, J=6.8Hz), 2.28(6H, s), 2.30(1H, m), 4.76(1H, d, J=16.7Hz), 5.12(1H, d, J=16.7Hz), 7.02(2H, m), 7.17(1H, s), 7.39(1H, s), 7.48(1H, s), 8.38(1H, d), 9.06(1H, s) |
| 115 | 202~205 | δ 1.04(3H, t), 2.25(6H, s), 2.70(2H, q), 5.20(2H, s), 6.70(2H, s), 6.84(1H, s), 7.20(1H, m), 7.55(1H, d), 8.48(1H, d), 8.53(1H, d), 9.12(1H, s) |
| 116 | 159~161 | δ 1.22(6H, d), 2.25(6H, s), 3.50(1H, m), 5.26(2H, s), 6.68(2H, s), 6.84(1H, s), 7.21(1H, m), 7.57(1H, s), 8.48(1H, d), 8.54(1H, s), 8.96(1H, s) |
| 117 | 230~232 | δ 0.91(3H, t), 2.17(2H, q), 2.28(6H, s), 4.93(2H, s), 6.50(2H, s), 6.77(1H, s), 7.25(1H, t), 7.70(1H, d), 8.54(2H, m), 9.15(1H, s) |
| 118 | 190~193 | δ 1.10(6H, d), 2.29(6H, s), 2.75(1H, m), 4.89(2H, s), 6.50(2H, s), 6.77(1H, s), 7.25(1H, t), 7.69(1H, d), 8.53(2H, m), 8.90(1H, s) |
| 119 | 170~172 | δ 0.95(3H, t), 2.01(1H, m), 2.24(1H, m), 2.31(6H, s), 4.73(1H, d), 4.90(1H, d), 7.13(1H, m), 7.26(2H, s), 7.34(1H, s), 7.51(1H, d), 8.29(1H, s), 8.41(1H, d), 9.09(1H, s) |
| 120 | 178~180 | δ 1.10(3H, d), 1.21(3H, d), 2.31(6H, s), 2.32(1H, m), 4.69(1H, d), 4.90(1H, d), 7.11(1H, m), 7.25(2H, s), 7.35(1H, s), 7.51(1H, d), 8.27(1H, d), 8.40(1H, d), 9.72(1H, s) |
| 121 | 145~148 | δ 1.14(3H, t), 2.36(6H, s), 2.56(2H, q), 5.17(2H, s), 7.01(1H, s), 7.05(1H, d), 7.18(4H, m), 7.56(1H, t) |
| 122 | 159~161 | δ 1.33(6H, d), 2.36(6H, s), 3.12(1H, m), 5.14(2H, s), 6.97(1H, s), 7.02(1H, s), 7.17(4H, m), 7.55(1H, m) |
| 123 | 199~201 | δ 0.95(3H, t), 2.20(2H, q), 2.24(6H, s), 5.07(2H, s), 6.49(2H, s), 6.69(1H, s), 7.03(1H, d), 7.13(1H, d), 7.53(1H, t), 8.84(1H, s) |
| 124 | 223~225 | δ 1.14(6H, d), 2.24(6H, s), 2.77(1H, m), 5.02(2H, s), 6.44(2H, s), 6.67(1H, s), 7.01(1H, d), 7.12(1H, d), 7.53(1H, t), 8.82(1H, s) |
| 125 | 196~198 | δ 0.96(3H, t), 2.04(1H, m), 2.26(1H, m), 2.32(6H, s), 4.73(1H, d, J=16.7Hz), 5.06(1H, d, J=16.7Hz), 7.01(1H, d), 7.07(1H, d), 7.23(1H, s), 7.43(2H, s), 7.48(1H, d), 8.90(1H, s) |
| 126 | 206~208 | δ 1.14(3H, d, J=6.8Hz), 1.21(3H, d, J=6.8Hz), 2.30(1H, m), 2.32(6H, s), 4.69(1H, d, J=16.9Hz), 5.04(1H, d, J=16.9Hz), 7.01(1H, d), 7.05(1H, d), 7.22(1H, s), 7.43(2H, s), 7.48(1H, t), 8.66(1H, s) |
| 127 | 201~203 | δ 0.95(3H, t), 2.19(2H, q), 2.25(6H, s), 5.07(2H, s), 6.47(2H, s), 6.69(1H, s), 7.07(1H, d), 7.29(1H, d), 7.43(1H, t), 8.68(1H, s) |
| 128 | 228~230 | δ 1.14(6H, d), 2.25(6H, s), 2.77(1H, m), 5.02(2H, s), 6.43(2H, s), 6.68(1H, s), 7.04(1H, d), 7.28(1H, d), 7.43(1H, t), 8.57(1H, s) |
| 129 | 215~217 | δ 0.97(3H, t), 2.04(1H, m), 2.26(1H, m), 2.33(6H, s), 4.74(1H, d, J=16.6Hz), 5.05(1H, d, J=16.6Hz), 7.05(1H, d), 7.23(2H, m), 7.38(3H, m), 8.86(1H, s) |
| 130 | 218~220 | δ 1.14(3H, d, J=6.8Hz), 1.21(3H, d, J=6.8Hz), 2.31(1H, m), 2.33(6H, s), 4.71(1H, d, J=17.0Hz), 5.04(1H, d, J=17.0Hz), 7.05(1H, d), 7.21(2H, m), 7.38(3H, m), 8.77(1H, s) |
| 131 | 107~110 | δ 1.16(3H, t), 2.36(6H, s), 2.58(2H, q), 5.40(2H, s), 7.01(1H, s), 7.15(1H, s), 7.21(1H, s), 7.48(1H, t), 7.65(1H, s), 7.75(1H, d), 8.08(2H, m) |
| 132 | 181~183 | δ 1.35(6H, d), 2.35(6H, s), 3.15(1H, m), 5.37(2H, s), 6.99(1H, s), 7.14(1H, s), 7.21(2H, s), 7.27(1H, s), 7.48(1H, t), 7.66(1H, s), 7.75(1H, d), 8.04(1H, d), 8.07(1H, d) |

-continued

| Ex. No. | m.p. (° C.) | NMR(¹H NMR(CDCl₃)) |
|---|---|---|
| 133 | 220~222 | δ 0.96(3H, t), 2.09(6H, s), 2.20(2H, q), 5.32(2H, s), 6.43(2H, s), 6.51(1H, s), 7.22(1H, d), 7.52(1H, t), 7.69(1H, t), 7.75(1H, d), 7.99(1H, d), 8.06(1H, d), 8.58(1H, s) |
| 134 | 246~248 | δ 1.14(6H, d), 2.11(6H, s), 2.78(1H, m), 5.24(2H, s), 6.40(2H, s), 6.52(1H, s), 7.18(1H, d), 7.49(1H, t), 7.67(1H, t), 7.74(1H, d), 7.94(1H, d), 8.04(1H, d), 8.66(1H, s) |
| 135 | 218~220 | δ 0.96(3H, t), 2.01(1H, m), 2.03(6H, s), 2.25(1H, m), 4.83(1H, d, J=16.0Hz), 5.49(1H, d, J=16.0Hz), 6.87(1H, s), 7.14(1H, d), 7.27(2H, s), 7.48(1H, t), 7.63(1H, t), 7.67(1H, d), 7.85(1H, d), 7.95(1H, d), 8.80(1H, s) |
| 136 | 152~154 | δ 1.12(3H, d, J=6.8Hz), 1.22(3H, d, H=6.8Hz), 2.03(6H, s), 2.30(1H, m), 4.79(1H, d, J=16.2Hz), 5.49(1H, d, J=16.2Hz), 6.85(1H, s), 7.14(1H, d), 7.26(2H, s), 7.48(1H, t), 7.62(1H, t), 7.67(1H, d), 7.84(1H, d), 7.94(1H, d), 8.59(1H, s) |
| 137-1 | 214~216 | δ 0.98(3H, t), 2.21(2H, q), 2.40(6H, s), 4.25(2H, d), 5.02(1H, m), 5.20(1H, s), 5.45(1H, m), 6.44(2H, s), 6.70(1H, s), 8.45(1H, s) |
| 137-2 | 153~155 | δ 0.95(3H, t), 2.22(2H, q), 2.31(6H, s), 2.58(1H, m), 2.77(1H, t), 3.17(1H, m), 3.86(1H, m), 4.11(1H, m), 6.57(2H, s), 6.79(1H, s), 8.95(1H, s) |
| 138-1 | 136~138 | δ 1.10(3H, s), 1.24(3H, s), 2.42(6H, s), 2.79(1H, m), 4.19(1H, d), 5.09(1H, m), 5.21(1H, s), 5.39(1H, m), 6.50(2H, s), 6.78(1H, s), 8.29(1H, s) |
| 138-2 | 172~174 | δ 1.15(3H, s), 1.19(3H, s), 2.31(6H, s), 2.58(1H, m), 2.77(2H, m), 3.16(1H, m), 3.82(1H, m), 3.96(1H, m), 6.55(2H, s), 6.84(1H, s), 9.06(1H, s) |
| 139-1 | 177~179 | δ 0.97(3H, t), 2.05(1H, m), 2.21(1H, m), 2.43(6H, s), 4.15(2H, m), 5.00(1H, m), 5.19(1H, s), 5.40(1H, m), 7.42(1H, s), 7.65(2H, s), 8.75(1H, s) |
| 139-2 | 188~190 | δ 0.98(3H, t), 2.05(1H, m), 2.28(1H, m), 2.41(6H, s), 2.51(1H, m), 2.71(1H, m), 3.09(1H, m), 3.56(1H, m), 3.87(1H, m), 7.36(1H, s), 7.54(2H, s), 9.12(1H, s) |
| 140-1 | 175~177 | δ 1.12(3H, d), 1.25(3H, d), 2.40(6H, s), 2.70(1H, m), 4.12(2H, m), 5.04(1H, m), 5.10(1H, s), 5.50(1H, m), 7.48(1H, s), 7.79(2H, s), 8.65(1H, s) |
| 140-2 | 163~165 | δ 1.14(3H, d), 1.23(3H, d), 2.36(1H, m), 2.41(6H, s), 2.46(1H, m), 2.70(1H, m), 3.08(1H, m), 3.55(1H, m), 3.84(1H, m), 7.37(1H, s), 7.56(2H, s), 9.26(1H, s) |
| 141 | 248~249 | δ 0.88(3H, t), 2.15(2H, q), 2.23(6H, s), 6.49(2H, s), 6.59(2H, s), 6.75(1H, s), 7.38(1H, t), 7.52(1H, t), 7.87(1H, d), 8.02(1H, d), 8.76(1H, s) |
| 142 | 278~279 | δ 1.07(6H, d), 2.24(6H, s), 2.74(1H, m), 6.51(2H, s), 6.54(2H, s), 6.74(1H, s), 7.38(1H, t), 7.52(1H, t), 7.87(1H, d), 8.01(1H, d), 8.72(1H, s) |
| 143 | 226~229 | δ 0.89(3H, t), 2.01(2H, m), 2.13(6H, br), 6.21(1H, d, J=14.5Hz), 6.90(1H, d, J=14.5Hz), 7.08(1H, s), 7.24(2H, s), 7.30(1H, t), 7.48(1H, t), 7.66(1H, d), 7.82(1H, d), 8.83(1H, s) |
| 144 | 246~247 | δ 1.00(3H, d, J=6.7Hz), 1.18(3H, d, J=6.7Hz), 2.12(6H, br), 2.28(1H, m), 6.27(1H, d, J=14.1Hz), 6.90(1H, d, J=14.1Hz), 7.10(1H, s), 7.26(2H, s), 7.32(1H, t), 7.48(1H, t), 7.68(1H, d), 7.84(1H, d), 8.83(1H, s) |
| 145 | 104~106 | δ 1.12(3H, t), 2.15(6H, s), 2.83(1H, q), 5.51(2H, s), 6.60(1H, s), 6.81(2H, s), 7.28(1H, m), 7.38(1H, m), 7.58(1H, m), 8.59(1H, s) |
| 146 | 107~109 | δ 1.30(6H, d), 2.15(6H, s), 3.64(1H, m), 5.49(2H, s), 6.60(1H, s), 6.80(2H, s), 7.30(2H, m), 7.39(1H, m), 7.58(1H, m), 8.96(1H, s) |
| 147 | 121~123 | δ 0.96(3H, t), 2.16(6H, s), 2.21(2H, q), 5.33(2H, s), 6.56(2H, s), 6.60(1H, s), 7.29(1H, m), 7.42(1H, m), 7.62(1H, m), 8.86(1H, s) |
| 148 | 200~202 | δ 1.14(3H, s), 1.15(3H, s), 2.15(6H, s), 2.78(1H, m), 5.22(2H, s), 6.49(2H, s), 6.54(1H, s), 7.29(2H, m), 7.43(1H, m), 7.63(1H, m), 9.25(1H, s) |
| 149 | 218~220 | δ 0.98(3H, t), 2.01(1H, m), 2.21(1H, m), 2.48(6H, s), 4.80(1H, d), 5.42(1H, d), 6.90(1H, m), 7.15(2H, m), 7.52(1H, m), 7.60(2H, m), 9.21(1H, s) |
| 150 | 138~140 | δ 1.15(3H, d), 1.17(3H, d), 2.20(6H, s), 2.52(1H, m), 4.88(1H, d), 5.40(1H, d), 6.98(1H, m), 7.20(2H, m), 7.43(2H, m), 7.52(2H, m), 9.01(1H, s) |
| 151 | 138~140 | δ 1.07(3H, t), 2.22(6H, s), 2.72(2H, q), 3.75(3H, s), 5.59(2H, s), 6.50(1H, d), 6.65(1H, s), 6.79(1H, s), 7.15(2H, d), 8.89(1H, s) |
| 152 | 135~137 | δ 1.12(6H, d), 2.22(6H, s), 3.52(1H, m), 3.80(3H, s), 5.64(2H, s), 6.51(1H, d), 6.64(1H, s), 6.79(1H, s), 7.17(1H, d), 8.42(1H, s) |
| 153 | 150~152 | δ 0.93(3H, t), 2.17(2H, q), 2.22(6H, s), 3.71(3H, s), 5.39(2H, s), 6.34(1H, d), 6.48(1H, s), 6.68(1H, s), 7.25(1H, d), 8.57(1H, s) |
| 154 | 157~159 | δ 1.12(6H, d), 2.22(6H, s), 2.75(1H, m), 3.71(3H, s), 5.35(2H, s), 6.33(2H, s), 6.47(1H, d), 6.67(1H, s), 7.24(1H, d), 8.85(1H, s) |
| 155 | 204~206 | δ 0.95(3H, t), 2.02(1H, m), 2.25(1H, m), 2.30(6H, s), 3.70(3H, s), 5.17(1H, d, J=17.1Hz), 5.35(1H, d, J=17.1Hz), 6.34(1H, d), 7.22(4H, m), 9.03(1H, s) |
| 156 | 180~183 | δ 1.12(3H, d, J=6.7Hz), 1.22(3H, d, J=6.7Hz), 2.30(1H, s), 2.31(1H, m), 3.71(3H, s), 5.14(1H, d, J=17.2Hz), 5.35(1H, d, J=17.2Hz), 6.31(1H, d), 7.21(4H, m), 9.00(1H, s) |
| 157 | 162~165 | δ 0.93(3H, t), 2.12(3H, s), 2.18(2H, q), 2.30(6H, s), 4.55(2H, s), 6.55(1H, s), 6.79(2H, s), 8.56(1H, s) |
| 158 | 181~183 | δ 1.13(3H, s), 1.14(3H, s), 2.10(3H, s), 2.31(6H, s), 2.40(6H, s), 2.77(1H, m), 4.50(2H, s), 6.53(2H, s), 6.78(1H, s), 8.91(1H, s) |
| 159 | 186~189 | δ 0.96(3H, t), 2.00(3H, s), 2.13(2H, br), 2.40(6H, s), 4.34(2H, br), 7.34(1H, s), 7.55(2H, s), 8.52(1H, s) |
| 160 | 181~183 | δ 1.21(3H, d), 1.31(3H, d), 1.98(3H, s), 2.31(1H, m), 2.40(6H, s), 4.24(2H, dd), 7.34(1H, s), 7.57(2H, s), 8.41(1H, s) |
| 161 | 116~118 | δ 0.94(3H, t), 1.04(3H, t), 2.19(2H, q), 2.30(6H, s), 2.35(2H, q), 4.53(2H, s), 6.54(2H, s), 6.78(1H, s), 8.43(1H, s) |
| 162 | 135~138 | δ 1.03(3H, t), 1.13(6H, d), 2.30(6H, s), 2.33(2H, q), 2.78(1H, m), 4.49(2H, s), 6.52(2H, s), 6.77(1H, s), 8.50(1H, s) |
| 163 | 124~126 | δ 0.91(3H, t), 0.96(3H, t) 2.22(4H, br), 2.39(6H, s), 4.51(2H, br), 7.33(1H, s), 7.54(2H, s), 8.53(1H, s) |
| 164 | 174~176 | δ 0.89(3H, t), 1.14(3H, d), 1.21(3H, d), 2.14(1H, m), 2.30(2H, m), 2.40(6H, s), 4.23(2H, dd), 7.33(1H, s), 7.55(2H, s), 8.67(1H, s) |
| 165 | 267~269 | δ 0.96(3H, t), 2.22(2H, q), 2.26(6H, s), 5.18(2H, s), 6.53(2H, s), 6.74(1H, s), 7.47(2H, t), 7.60(1H, t), 7.85(2H, d), 8.40(1H, s) |
| 166 | 238~241 | δ 1.16(3H, s), 1.17(3H, s), 2.25(6H, s), 2.80(1H, m), 5.12(2H, s), 6.49(2H, s), 6.73(1H, s), 7.46(2H, t), 7.60(1H, t), 7.83(2H, d), 8.37(1H, s) |
| 167 | 246~248 | δ 0.98(3H, t), 2.22(2H, br), 2.35(6H, s), 4.89(2H, br), 7.25(1H, s), 7.40(2H, t), 7.55(3H, m), 7.72(2H, d), 8.57(1H, s) |
| 168 | 245~247 | δ 1.16(3H, d, J=6.65Hz), 1.23(3H, d, J=6.65Hz), 2.32(1H, m), 2.35(6H, s), 4.78(1H, d, J=17.5Hz), 5.11(1H, d, J=17.5Hz), 7.25(1H, s), 7.39(2H, t), 7.55(3H, m), 7.70(2H, d), 8.37(1H, s) |

Activity and Toxicity

Anti-HIV activity tests in vitro of the compounds according to the present invention were performed as described in J. Med. Chem, 34, 357, 1991. Inhibition by the compounds of virus-induced cytotoxic effect in MT-4 cells was measured as follows.

MT-4 cells were suspended in culture media at $2.5 \times 10^5$ cells/ml and infected with 1000 $CCID_{50}$ (50% cell culture infective dose) of HIV. Immediately after virus infection, 100 μl of cell suspension was brought into each well of a flat-bottomed microtitray containing various concentrations of the test compounds. After 4 or 5 days incubation at 37° C., efficacy of the compounds was determined by the MTT method. Cytotoxicity of the compounds was assessed in parallel with their antiviral activity, based on viability of mock-infected host cells as determined by the MTT method.

The results are shown in the following table.

| No. of Example | $CD_{50}$ (µg/ml) | $ED_{50}$ (µg/ml) | S.I. ($CD_{50}/ED_{50}$) |
|---|---|---|---|
| 1 | 4.75 | 0.0027 | 1,740 |
| 2 | 12.43 | <0.0002 | >621,500 |
| 3 | >100.00 | 0.011 | >9,115 |
| 4 | 12.70 | <0.0002 | >635,000 |
| 5 | 39.4 | 0.0011 | 35,438 |
| 6 | 8.5 | 0.0022 | 3,895 |
| 7 | 11.73 | 0.028 | 412 |
| 8 | 5.9 | 0.013 | 459 |
| 9 | >100.00 | 0.0756 | >9,115 |
| 10 | 7.8 | 0.0147 | 527 |
| 11 | 89.1 | 0.0027 | 32,753 |
| 12 | 8.5 | 0.0027 | 3,110 |
| 13 | 11.10 | 0.27 | 41 |
| 14 | 6.40 | 0.061 | 105 |
| 15 | 9.17 | 0.069 | 133 |
| 16 | 8.30 | 0.065 | 128 |
| 17 | 7.10 | 0.013 | 546 |
| 18 | 8.00 | 0.013 | 598 |
| 19 | 12.59 | 0.015 | 837 |
| 20 | 11.30 | 0.012 | 909 |
| 21 | 16.58 | 0.036 | 459 |
| 22 | 25.48 | 0.015 | 1,710 |
| 23 | 8.00 | 0.0016 | 4,872 |
| 24 | 5.20 | 0.0009 | 5,689 |
| 25 | 9.04 | 0.003 | 3,639 |
| 26 | 9.53 | 0.003 | 3,504 |
| 27 | 10.68 | 0.014 | 772 |
| 28 | 30.60 | 0.006 | 4,856 |
| 29 | 7.22 | 0.003 | 2,414 |
| 30 | 3.83 | 0.002 | 1,784 |
| 31 | 4.86 | 0.017 | 285 |
| 32 | 8.99 | 0.017 | 520 |
| 33 | >100.00 | 0.069 | >1,458 |
| 34 | 8.06 | 0.045 | 180 |
| 35 | 33.83 | 0.004 | 8,672 |
| 36 | 7.88 | 0.005 | 1,670 |
| 37 | >100.00 | 0.043 | >2,328 |
| 38 | >100.00 | 0.082 | >1,215 |
| 39 | 60.47 | 0.619 | 98 |
| 40 | >100.00 | >100.00 | ND |
| 41 | 2.56 | 0.003 | 800 |
| 42 | >100.00 | 0.005 | >21,852 |
| 43 | 1.77 | 0.015 | 118 |
| 44 | 8.88 | 0.008 | 1,056 |
| 45 | >100.00 | 0.061 | >1,630 |
| 46 | 9.20 | 0.023 | 409 |
| 47 | 2.53 | 0.003 | 849 |
| 48 | 8.07 | 0.003 | 2,649 |
| 49 | 7.48 | 0.014 | 531 |
| 50 | 8.70 | 0.015 | 578 |
| 51 | 8.01 | 0.13 | 64 |
| 52 | 8.20 | 0.098 | 84 |
| 53 | 2.50 | 0.014 | 179 |
| 54 | 7.10 | 0.014 | 502 |
| 55 | 10.8 | 0.071 | 145 |
| 56 | 11.34 | 0.21 | 54 |
| 57 | 36.80 | 1.37 | 27 |
| 58 | >100.00 | 0.51 | >195 |
| 59 | 69.00 | 0.31 | 224 |
| 60 | 12.09 | 0.23 | 52 |
| 61 | >100.00 | >100.00 | ND |
| 62 | >100.00 | >100.00 | ND |
| 63 | >100.00 | >100.00 | ND |
| 64 | >100.00 | >100.00 | ND |
| 65 | >100.00 | >100.00 | ND |
| 66 | 8.14 | 1.75 | 5 |
| 67 | 12.40 | 0.008 | 1,654 |
| 68 | 4.15 | 0.005 | 907 |
| 69 | >100.00 | 0.034 | >2,922 |
| 70 | >100.00 | 0.014 | >7,210 |
| 71 | >100.00 | 0.004 | >28,470 |
| 72 | 5.26 | 0.003 | 1,933 |
| 73 | >100.00 | 0.016 | >6,250 |
| 74 | 10.50 | 0.013 | 788 |
| 75 | 14.30 | >14.26 | <1 |
| 76 | 12.10 | 0.022 | 563 |
| 77 | 7.0 | 0.003 | 2,367 |
| 78 | 7.1 | 0.0033 | 2,140 |
| 79 | 24.77 | 0.052 | 476 |
| 80 | 46.83 | 0.049 | 958 |
| 81 | >100.00 | 1.162 | >86 |
| 82 | 36.15 | 0.173 | 209 |
| 83 | 3.10 | 0.021 | 147 |
| 84 | 7.88 | 0.024 | 324 |
| 85 | 13.17 | 0.13 | 102 |
| 86 | 2.11 | 0.094 | 22 |
| 87 | >100.00 | 2.05 | >48 |
| 88 | >100.00 | 0.42 | >240 |
| 89 | 8.75 | 0.09 | 98 |
| 90 | 8.90 | 0.12 | 73 |
| 91 | 1.27 | 0.004 | 328 |
| 92 | 8.93 | 0.013 | 698 |
| 93 | 83.22 | 0.013 | 6,380 |
| 94 | 8.20 | 0.015 | 538 |
| 95 | 16.50 | 0.013 | 1,239 |
| 96 | 9.64 | 0.014 | 713 |
| 97 | 0.59 | >0.59 | <1 |
| 98 | 1.75 | >1.75 | <1 |
| 99 | 4.12 | >4.12 | <1 |
| 100 | 2.02 | >2.02 | <1 |
| 101 | 0.94 | >0.94 | <1 |
| 102 | 4.44 | >4.44 | <1 |
| 103 | 85.19 | >85.19 | <1 |
| 104 | >100.00 | >100.00 | ND |
| 105 | 5.30 | 0.52 | 10 |
| 106 | 9.49 | 0.49 | 19 |
| 107 | 2.38 | 0.026 | 92 |
| 108 | 14.41 | 0.017 | 852 |
| 109 | 29.72 | 0.015 | 1,972 |
| 110 | 9.61 | 0.009 | 1,109 |
| 111 | >100.00 | 0.081 | >1,223 |
| 112 | >100.00 | 0.029 | >3,403 |
| 113 | 32.80 | 0.0084 | 3,914 |
| 114 | 24.60 | 0.0032 | 7,713 |
| 115 | 16.63 | 0.014 | 1,173 |
| 116 | 10.09 | 0.003 | 3,945 |
| 117 | 40.20 | 0.061 | 660 |
| 118 | 33.50 | 0.015 | 2,201 |
| 119 | 39.00 | 0.0038 | 10,248 |
| 120 | 8.80 | 0.002 | 4,044 |
| 121 | 7.72 | >7.72 | <1 |
| 122 | 2.80 | >2.80 | <1 |
| 123 | 79.14 | 0.122 | 649 |
| 124 | >100.00 | 0.082 | >1,223 |
| 125 | 9.02 | 0.015 | 591 |
| 126 | 9.85 | 0.011 | 887 |
| 127 | 9.46 | 0.194 | 49 |
| 128 | 48.27 | 0.079 | 610 |
| 129 | 7.44 | 0.010 | 720 |
| 130 | 8.85 | 0.015 | 577 |
| 131 | 10.60 | >10.6 | <1 |
| 132 | 9.60 | >9.58 | <1 |
| 133 | 11.70 | 0.060 | 193 |
| 134 | 66.80 | 0.004 | 1,691 |
| 135 | 6.80 | 0.0089 | 764 |
| 136 | 8.70 | 0.0097 | 905 |
| 137 | 40.50 | 1.25 | 32 |
| 138 | 39.60 | 0.34 | 118 |
| 139 | >100.00 | 0.34 | >299 |
| 140 | 41.90 | 0.094 | 444 |
| 141 | 27.60 | 0.11 | 255 |
| 142 | >100.00 | 0.044 | >2,296 |
| 143 | 9.76 | 0.026 | 373 |
| 144 | 8.89 | 0.030 | 298 |
| 145 | >100.00 | 3.04 | >33 |
| 146 | >100.00 | 1.02 | >98 |
| 147 | 40.20 | 0.061 | 660 |
| 148 | 9.00 | 0.010 | 875 |
| 149 | 6.78 | 0.029 | 2,302 |
| 150 | 7.09 | 0.0031 | 2318 |
| 151 | 8.67 | 0.015 | 587 |
| 152 | 9.61 | 0.018 | 546 |

-continued

| No. of Example | CD$_{50}$(μg/ml) | ED$_{50}$(μg/ml) | S.I.(CD$_{50}$/ED$_{50}$) |
|---|---|---|---|
| 153 | 12.22 | 0.278 | 44 |
| 154 | 10.11 | 0.074 | 137 |
| 155 | 13.45 | 0.017 | 793 |
| 156 | 10.92 | 0.014 | 810 |
| 157 | 3.6 | 0.0119 | 304 |
| 158 | >100.00 | 0.0043 | >23,240 |
| 159 | 11.8 | 0.0018 | 6,628 |
| 160 | 14.0 | 0.0005 | 29,796 |
| 161 | 48.0 | 0.018 | 2,669 |
| 162 | 41.40 | 0.0159 | 2,611 |
| 163 | 9.31 | 0.0034 | 2,745 |
| 164 | 20.58 | 0.0026 | 8,053 |
| 165 | 58.11 | >58.11 | <1 |
| 166 | >100.00 | 0.7562 | >132 |
| 167 | 43.31 | 0.0569 | 761 |
| 168 | 5.48 | 0.0174 | 315 |
| AZT | 0.70 | 0.0015 | 604 |

Usefulness of the Invention

The present compounds have strong anti-HIV activity as well as very low toxicity, and thus they are expected to be used as potent antiviral agents.

What is claimed is:

1. A compound of formula (I) or a pharmaceutically acceptable salt thereof:

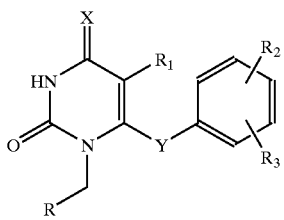

(I)

wherein

R represents cyclopropyl; cyclobutyl, 1- or 2-naphthyl; 9-anthracenyl; 2-anthraquinonyl; 2-, 3- or 4-quinolinyl; oxiranyl; 1-benzotriazolyl; 2-benzoxazolyl; furanyl substituted with $C_1$–$C_4$ alkoxycarbonyl; $C_1$–$C_4$ alkylcarbonyl; or benzoyl, $R_1$ represents halogen or $C_1$–$C_4$ alkyl, $R_2$ and $R_3$ represent independently hydrogen or $C_1$–$C_4$ alkyl, X represents oxygen atom, and Y represents oxygen atom, sulfur atom or carbonyl.

2. The compound according to claim 1, wherein $R_1$ is ethyl or isopropyl, and $R_2$ and $R_3$ are methyl.

3. A process for the preparation of the compound of formula (I) according to claim 1, by reacting a compound of formula (II) and a compound of formula (III)

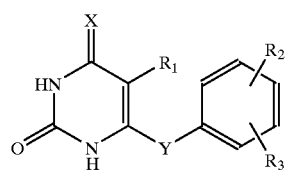

(II)

R—Lie (III)

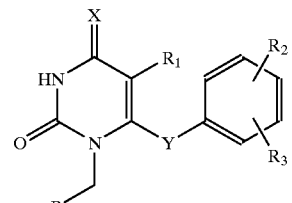

(I)

wherein, R, $R_1$, $R_2$, $R_3$, X and Y are as defined in claim 1, and Lie represents a leaving group.

4. The process according to claim 3, wherein the reaction is performed in a polar organic solvent in the presence of a base, at a temperature of 10~100° C., for 1~48 hours, and with a ratio of 1:0.8~1:3 of the compound of formula (II) and the compound of formula (III).

5. A pharmaceutical composition, comprising: an antiviral-effective amount of the compound of formula (I) according to claim 1 or a pharmaceutically acceptable salt thereof and pharmaceutically acceptable vehicles.

* * * * *